US012653770B2

(12) United States Patent (10) Patent No.: US 12,653,770 B2
Sandmeyer et al. (45) Date of Patent: Jun. 16, 2026

(54) METHOD FOR PRODUCING HYDROPHILIC ORGANOPOLYSILOXANE GELS

(71) Applicant: WACKER CHEMIE AG, Munich (DE)

(72) Inventors: Frank Sandmeyer, Burgkirchen (DE); Bernd-Josef Bachmeier, Haiming (DE)

(73) Assignee: Wacker Chemie AG, Munich (DE)

( * ) Notice: Subject to any disclaimer, the term of this patent is extended or adjusted under 35 U.S.C. 154(b) by 606 days.

(21) Appl. No.: 18/026,837

(22) PCT Filed: Sep. 24, 2020

(86) PCT No.: PCT/EP2020/076786
§ 371 (c)(1),
(2) Date: Mar. 17, 2023

(87) PCT Pub. No.: WO2022/063405
PCT Pub. Date: Mar. 31, 2022

(65) Prior Publication Data
US 2023/0331919 A1 Oct. 19, 2023

(51) Int. Cl.

| | |
|---|---|
| *A61K 8/891* | (2006.01) |
| *A61K 8/04* | (2006.01) |
| *A61Q 17/02* | (2006.01) |
| *A61Q 19/10* | (2006.01) |
| *C08G 77/08* | (2006.01) |
| *C08G 77/12* | (2006.01) |
| *C08G 77/20* | (2006.01) |
| *C08L 83/04* | (2006.01) |

(52) U.S. Cl.
CPC .............. *A61K 8/891* (2013.01); *A61K 8/042* (2013.01); *A61Q 17/02* (2013.01); *A61Q 19/10* (2013.01); *C08G 77/08* (2013.01); *C08G 77/12* (2013.01); *C08G 77/20* (2013.01); *C08L 83/04* (2013.01)

(58) Field of Classification Search
CPC ................................. C08L 83/06; A61K 8/894
See application file for complete search history.

(56) References Cited

U.S. PATENT DOCUMENTS

| | | | |
|---|---|---|---|
| 5,654,362 A | 8/1997 | Schulz, Jr. et al. | |
| 5,831,080 A | 11/1998 | Sejpka et al. | |
| 5,859,069 A * | 1/1999 | Yanagida ............... | A61K 8/894 |
| | | | 424/78.03 |
| 6,200,581 B1 | 3/2001 | Lin et al. | |
| 6,365,670 B1 * | 4/2002 | Fry .......................... | C08L 83/04 |
| | | | 514/846 |
| 6,423,322 B1 | 7/2002 | Fry | |
| 6,881,416 B2 | 4/2005 | Fry | |
| 10,933,011 B2 * | 3/2021 | Li ........................... | A61K 8/894 |
| 2008/0199417 A1 | 8/2008 | Joffre et al. | |
| 2010/0183525 A1 * | 7/2010 | Lin .......................... | A61K 8/31 |
| | | | 424/59 |
| 2012/0202895 A1 | 8/2012 | Ikeda | |
| 2013/0115184 A1 | 5/2013 | Beck et al. | |
| 2016/0311980 A1 | 10/2016 | Knoer | |
| 2016/0317427 A1 | 11/2016 | Knoer | |
| 2018/0078486 A1 * | 3/2018 | Kadlec ................... | A61Q 19/00 |
| 2021/0145727 A1 * | 5/2021 | Sandmeyer ............ | A61Q 15/00 |
| 2022/0089873 A1 * | 3/2022 | Mitra .................. | C08B 37/0012 |

FOREIGN PATENT DOCUMENTS

| | | | | |
|---|---|---|---|---|
| EP | 381166 A | * | 8/1990 | |
| JP | 02243612 A | * | 9/1990 | |
| WO | 2013096325 A1 | | 6/2013 | |
| WO | 2018228657 A1 | | 12/2018 | |
| WO | WO 2018/228657 | * | 12/2018 | |
| WO | 2020139403 A1 | | 7/2020 | |

OTHER PUBLICATIONS

Ullmann's Encyclopedia of Industrial Chemistry, CD-ROM edition 2003, Wiley-VCH Verlag, "Emulsions".

* cited by examiner

*Primary Examiner* — Marc S Zimmer

(57) ABSTRACT

Hydrophilic organopolysiloxane gel preparations, methods for making and uses for the hydrophilic organopolysiloxane gel preparations.

15 Claims, No Drawings

METHOD FOR PRODUCING HYDROPHILIC ORGANOPOLYSILOXANE GELS

CROSS-REFERENCE TO RELATED APPLICATIONS

This application is a U.S. National Phase application of PCT Application NO. PCT/EP2020/076786 filed on Sep. 24, 2020, which is incorporated by reference herein in its entirety.

The invention relates to hydrophilic organopolysiloxane gels, to a process for preparing them and to their use in cosmetic compositions.

Organopolysiloxane gels may be prepared by crosslinking an unsaturated organopolysiloxane with an Si—H-containing organopolysiloxane, also referred to hereinafter as Si—H-functional crosslinker, in the presence of a diluent.

Crosslinks are connections of polymer chains in a three-dimensional network. They may be considered to be long-chain branches which are so numerous that a continuous insoluble network or gel is formed.

Organopolysiloxane networks are frequently prepared via platinum-catalysed hydrosilylation reactions. Frequently these reactions see an Si—H-containing organopolysiloxane brought to reaction with a vinyl-functional organopolysiloxane. A key prerequisite for the construction of a 3-dimensional network in this case is that at least one of the two components, the Si—H-containing organopolysiloxane or the vinyl-functional organopolysiloxane, has more than two functionalities per molecule in the average composition.

In the development of organopolysiloxane networks, the platinum-catalysed hydrosilylation reaction affords the advantage that no by-products are formed and that linkage sites and network architecture are closely defined.

The most important reasons for using organopolysiloxane gels in cosmetic applications are the resultant sensorial advantages, especially the improvement of the skin feel of cosmetic formulations. Furthermore, organopolysiloxane gels act as thickeners in cosmetic formulations.

U.S. Pat. No. 6,423,322 B1 discloses organopolysiloxane gels, which can be easily prepared by hydrosilylation reaction of a specific, vinyl-functional MQ resin with an Si—H-containing organopolysiloxane in the presence of a diluent and of a small amount of platinum hydrosilylation catalyst in a thermal process, i.e. with heating to a temperature below the boiling point of the diluent used.

U.S. Pat. No. 5,654,362 teaches silicone gels for cosmetic applications which are obtained by hydrosilylation reactions of alpha-omega dienes with terminally and/or chain-internally Si—H-functional linear polyorganosiloxanes. The hydrosilylation takes place using a suitable catalyst in a solvent which may itself be a polyorganosiloxane.

US20120202895 A1 teaches a pastelike preparation for cosmetic applications, obtained by the hydrosilylation of one or more Si—H-containing polyorganosiloxanes with one or more aliphatically unsaturated polyorganosiloxanes in a solvent oil which is liquid at 25° C. In this case the polyorganosiloxanes used are exclusively linear polyorganosiloxanes, not resins. At least two of the polyorganosiloxanes used from the group of the Si—H-containing and unsaturated linear polyorganosiloxanes must have a chain length of more than 30 repeating units in order that there is no oily, greasy skin feel in use.

A factor common to these processes is that the crosslinked gel structures obtained are exclusively hydrophobic.

US2016311980A1 describes a process for preparing organopolysiloxane gels, containing glycoside radicals, from an unsaturated polyorganosiloxane resin, a glycoside radical containing a hydrosilylatable end group, and one or more Si—H-functional organopolysiloxanes, in a diluent in the presence of a hydrosilylation catalyst. The Si—H-containing crosslinkers here have preferably low Si—H-contents. They are able to absorb hydrophilic substances such as water or glycols without losing their viscous gel structure. The gels of the invention are prepared preferably in a two-stage process, with the hydrophilic component, that is to say the glycoside, being hydrosilylated in the first step and the hydrophobic component, that is to say the silicone resin, in the second step.

US20160317427A1 describes a process for preparing organopolysiloxane gels containing polyether radicals from an unsaturated polyorganosiloxane resin, polyoxyalkylated, terminally unsaturated alcohols with mixtures of Si—H-functional organopolysiloxanes in a diluent in the presence of a hydrosilylation catalyst. The Si—H-containing crosslinkers here have preferably low Si—H-contents. They are able to absorb hydrophilic substances such as water or glycols without losing their viscous gel structure. The gels of the invention are prepared preferably in a two-stage process, with the hydrophilic component, that is to say the polyglycol, being hydrosilylated in the first step and the hydrophobic component, that is to say the silicone resin, in the second step.

A factor common to these processes is that the crosslinked gel structures obtained are exclusively hydrophilic.

If the aim is to prepare a hydrophobic elastomer gel or a hydrophilic elastomer gel in the manner described above, a separate synthesis for each is required, and the resulting gel has either hydrophilic or hydrophobic properties. The gradation of the extent of the respective property—hydrophilic or hydrophobic—as well is set unambiguously by the synthesis of the respective compound.

For economic reasons it would be advantageous to be able to adjust and grade the hydrophilic or hydrophobic properties selectively by suitable blending of corresponding components in the manner of a modular system. At the same time, it is necessary to retain the other properties usually required of elastomer gels, such as, for example, good skin feel, clarity and creaminess as a result of a stable viscous gel structure, in both the hydrophobic and the hydrophilic modifications of the respective mixtures.

Moreover, the mixtures must be able to be prepared in a simple way. In everyday operation, this requirement cannot be achieved by the mixing of two high-viscosity gels, since because of their viscosity one alternative is that they must be combined manually, and this makes no sense either from the cost aspect or from the standpoint of industrially relevant production rates. They must be pumped into one another, and the connecting lines through which the pumping procedure takes place must subsequently be cleaned at suitable cost and effort, since high-viscosity gels cannot be removed from conduits simply by flushing with low-viscosity liquids. Low-viscosity cleaning liquids make channels through high-viscosity gels, and the liquids flow through these channels without removing the gel itself. With increasingly high-viscosity cleaning media or by dismantling of the conduits and manual cleaning, removal is possible, but this quite obviously entails in turn a suitable cost and effort and would ultimately provide a vanishingly small economic advantage, or none at all, relative to the synthesis of separate elastomer gels. And the cleaning solutions would have to be disposed of subsequently. An economic process cannot have these disadvantages.

U.S. Pat. No. 5,831,080 describes organosilicon compounds containing glycoside radicals, and a process for preparing them.

US20130115184A1 describes innovative saccharide siloxane copolymers and processes for preparing them.

They are used respectively as surfactants and emulsifiers or for improving the properties of cosmetic formulations.

US20080199417A1 teaches saccharide siloxanes, their preparation and their use for improving the properties of cosmetic preparations.

A factor common to these three specifications is that they are not elastomer gels but rather different silicon compounds, and they disclose the use thereof in cosmetic compositions, for example, where these silicon compounds have the function, for example, of surfactants, emulsifiers and foam stabilizers.

The object was to provide a simple modular system which with a minimal synthesis cost and complexity permits the preparation selectively of hydrophobic and hydrophilic elastomer gels for cosmetic applications and which does not have the disadvantages referred to above.

Surprisingly it has been found that the stated object is achieved by the hydrophilic organopolysiloxane gel preparation of the invention. It comprises 2 to 80 wt % of a mixture (X) of 80 to 99.9 wt % of at least one hydrophobic organopolysiloxane gel prepared by a process disclosed in the description, 0.1 to 20 wt % of at least one compound (3) selected from the group containing (3a) organopolysiloxanes containing glycoside radicals and of the general formula (V), $$R_h R^3{}_i SiO_{(4-h-i)/2} \qquad (V),$$

where

R may be identical or different and is a monovalent, optionally substituted hydrocarbon radical having 1 to 18 carbon atoms per radical, with exclusion of heteroatoms and hetero groups which would hinder a hydrosilylation reaction by adversely affecting the catalyst, $R^3$ may be identical or different and is a radical of the formula $$Z-(R^4O)_j-R^5- \qquad \text{(Va), in which}$$

Z is a glycoside radical composed of 1 to 10 monosaccharide units, preferably glucose units, $R^4$ may be identical or different and is a divalent hydrocarbon radical having 2 to 4 carbon atoms, j is 0 or an integer from 1 to 20, and $R^5$ may be identical or different and is a divalent hydrocarbon radical having 2 to 12 carbon atoms, h and i are each 0, 1, 2 or 3, with the proviso that h+i≤3 and in at least one repeating unit i has a value of at least 1;

(3b) organopolysiloxanes containing polyglycol radicals and of the formula (VI)

$$R_h R^6{}_i SiO_{(4-h-i)/2} \qquad (VI),$$

where

R has the definition indicated above, $R^6$ may be identical or different and is a radical of the formula $$P-R^7-R^8- \qquad \text{(VIa), in which}$$

P is a polyoxyalkylated radical of the type $-(OC_nH_{2n})_m-OH,$ $R^7$ is a chemical bond or a divalent hydrocarbon radical having 1 to 10 carbon atoms, preferably a radical of the formula $-CH_2-$, $-CH(CH_3)-$ or $-C(CH_3)_2-$, more preferably a radical of formula $-CH_2-$, and n is an integer from 1 to 4, preferably 2 or 3, and m is a positive integer, preferably from 1 to 40, $R^8$ is a divalent hydrocarbon radical having 2 to 12 carbon atoms, preferably a radical of the formula $-CH_2-CH_2-$, $-CH_2-CH(CH_3)-$ or $-CH_2-C(CH_3)_2-$, more preferably a radical of the formula $-CH_2-CH_2-$, h and i each have the definition indicated earlier on above;

(3c) organopolysiloxanes containing cyclodextrin radicals and of the formula (VII)

$$R_h R^9{}_i SiO_{(4-h-i)/2} \qquad (VII),$$

where

R may have the definitions indicated above, $R^9$ may be identical or different and is a radical of the formula $$C-R^{10}- \qquad \text{(VIIa), in which}$$

C is a cyclodextrin radical of the form

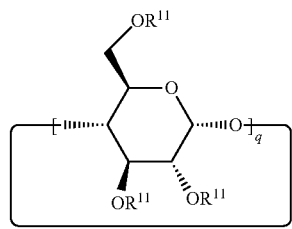

in which $R^{11}$ is a hydrogen radical or a methyl radical, and q is the integers 6 (alpha cyclodextrin), 7 (beta cyclodextrin) or 8 (gamma cyclodextrin), $R^{10}$ is a divalent hydrocarbon radical having 2 to 18 carbon atoms which is optionally interrupted with heteroatoms, h and i each have the definition indicated earlier on above;

where the sum of the mixture (X) always makes 100 wt %;

and 20 to 98 wt % of at least one diluent (4) for viscosity adjustment, which is different from (3a), (3b) and (3c);

where the hydrophilic organopolysiloxane gel preparation exhibits an increase in the water absorption capacity by at least a factor of 10, compared with the hydrophobic organopolysiloxane gel used;

and where the sum of the mixture (X) and the diluent (4) always makes 100 wt % of the hydrophilic organopolysiloxane gel preparation.

The amounts of compound (3) here which are needed to convert a hydrophobic gel into a hydrophilic gel of the invention are surprisingly low. It has emerged that the admixing of excessive amounts of compound (3) is damaging, as it may result in the partial or complete loss of the high-viscosity, creamy gel consistency. Details of this are given later on below in the detailed description of the invention, and illustrated with examples.

The change in property from hydrophobic to hydrophilic is determined here by the capacity of the resulting gel to absorb water. The capacity for water absorption of a hydrophobic gel increases continuously in line with the addition of compounds (3). An increase in the water absorption capacity of a hydrophobic gel by a factor of 10 is deemed to be significant and therefore essential for the change in property from hydrophobic to hydrophilic. Smaller water absorption amounts are possible, but for the present invention are not inventive and are therefore excluded as a subject of the invention.

It is surprising in particular that the hydrophilic organopolysiloxane gel preparations that are the subject of the invention, composed of hydrophobic starting gels with the same amount of hydrophilic groups in the mixture, are able to absorb at least as much water as elastomer gels prepared exclusively as hydrophilic elastomer gels, despite the fact that the hydrophilic organopolysiloxane gel preparations of the invention are merely physical mixtures of a hydrophobic elastomer gel with an organopolysiloxane of the compound (3) containing hydrophilic groups.

Hydrophobic Organopolysiloxane Gels (Also Referred to as Hydrophobic Elastomer Gels)

The mixture (X) contains 80 to 99.9 wt % of hydrophobic organopolysiloxane gels, preferably 85 to 99.8 wt %, more preferably 90 to 99.7 wt %.

The hydrophobic organopolysiloxane gels are those obtained from the reaction either of an unsaturated organopolysiloxane resin (1a) or of an unsaturated organopolysiloxane (1b) or of a diene (1c) with an Si—H-containing organopolysiloxane (2a) optionally in the mixture with an Si—H-containing organopolysiloxane (2b) in the presence of a catalyst (K) which promotes the addition of Si-bonded hydrogen onto aliphatic multiple bond (i.e. hydrosilylation catalyst) in the presence of a diluent (4), the reaction being stopped by addition of a stopper compound (5) which is used as a catalyst poison and which remains in the hydrophobic organopolysiloxane gel.

In the selection of the two Si—H-functional organopolysiloxanes, it may be appropriate to take account of the findings and framework conditions of WO2018228657A.

Also possible are gels of the kind described, for example, in U.S. Pat. No. 6,881,416B2, for which in the first step an unsaturated organic component having only one double bond (1c) is hydrosilylated, with only some of the Si—H groups of the Si—H-containing organopolysiloxane (2a), optionally in the mixture with an Si—H-containing organopolysiloxane (2b), being consumed and the rest of the Si—H functions being available for hydrosilylation reactions with an unsaturated organopolysiloxane resin (1a) as in U.S. Pat. No. 6,881,416B1 or else, in principle, with an unsaturated organopolysiloxane (1b).

It should be noted here that neither the hydrophobic organopolysiloxane gels nor the processes for preparing them are subjects of the invention here. They are all known from the prior art to a person of ordinary skill in the art and are consequently not claimed here. Since, however, they are vital to the explanation and the understanding of the invention, they are described in detail below.

Unsaturated organopolysiloxane resins (1a) are composed of units of the general formula (I)

$$R_xR^1_ySiO_{(4-x-y)/2} \tag{I}$$

where

R may be identical or different and is a monovalent, optionally substituted hydrocarbon radical having 1 to 18 carbon atoms per radical, with the exclusion of heteroatoms and hetero groups, which would hinder a hydrosilylation reaction by adversely affecting the catalyst, $R^1$ is a monovalent hydrocarbon radical onto which Si—H groups can be added in a hydrosilylation reaction, preferably a monovalent hydrocarbon radical having 2 to 18 carbon atoms and containing a terminal, aliphatic C—C multiple bond, more preferably an □-alkenyl radical having 2 to 12 carbon atoms, very preferably a vinyl radical, x is 0, 1, 2 or 3, y is 0, 1 or 2, preferably 0 or 1, with the proviso that the sum x+y is less than or equal to 3, and that per molecule there must be at least 2 radicals R', preferably at least 3 radicals R', at least mol % of T and/or Q units (T units: sum x+y=1; Q units: sum x+y=0), preferably at least mol % of Q units, and additionally D units (sum x+y=2) may be present.

The unsaturated organopolysiloxane resins of the formula (I) are preferably MQ resins composed of units of the formulae $$SiO_2 \text{ (Q units) and}$$

$$R_3SiO_{1/2} \text{ and } R^2R^1SiO_{1/2} \text{ (M units),}$$

where R and $R^1$ have the definition indicated for them above.

The molar ratio of M to Q units here is preferably in the range from 0.5 to 4.0, more preferably in the range from 0.5 to 2.0, very preferably in the range from 0.6 to 1.5. These silicone resins may additionally contain up to 10 wt % of free hydroxyl or alkoxy groups.

Unsaturated organopolysiloxanes (1b) are organopolysiloxanes of the general formula (II)

$$R^1_cR_{3-c}SiO(R_2SiO)_a(R_{2-d}R^1_dSiO)_bSiR_{3-c}R^1_c \tag{II},$$

where c is 0 or 1, preferably 1, d is 0 or 1, preferably 0,

R and $R^1$ have the definitions indicated for them above, a and b are integers, with the proviso that a+b=25-700, preferably 30-500, more particularly 40-300, especially 45-160, the values at the margins being included in each case, so that the unsaturated organopolysiloxanes (1b) contain preferably 2 terminally located unsaturated groups; a greater number of unsaturated groups may also be present, and they may be situated terminally or internally within the chain.

Unsaturated monoolefins (1c) are hydrosilylatable hydrocarbons which comprise at least 4 carbon atoms, preferably at least 5 carbon atoms, very preferably at least 6 carbon atoms, more particularly at least 7 carbon atoms. It is particularly preferred here for the monoolefin (1c) to contain 8-24 carbon atoms, more particularly 8-20 carbon atoms. The monoolefins (1c) may be linear, branched or cyclic. Nonlimiting examples are 1-butene, 1-pentene, 2-butene, 2-pentene, 1-hexene, 2-hexene, 3-hexene, 1-octene, isooctene, 1-decene, 1-dodecene, cyclohexene, methylcyclohexene, hexylcyclohexene, norbornene, camphene, 1-octadecene, etc.

Si—H-containing polyorganosiloxanes (2a) are Si—H functional organopolysiloxanes of the general formula (III)

$$H_eR_{3-e}SiO(R_2SiO)_f(RHSiO)_gSiR_{3-e}H_e \tag{III},$$

where e is 0 or 1, preferably 0,

R has the definition indicated for it above, f and g are integers, with the proviso that the sum f+g is 8 to 1000, preferably 20 to 750, and that the organopolysiloxanes (2a) contain Si-bonded hydrogen in amounts of 0.010 to 1.60 wt %, preferably of 0.010-1.30 wt %, more preferably of 0.010-1.25 wt %, more particularly of 0.010-0.60 wt %.

Preferred Si—H-containing polyorganosiloxanes (2a) are Si—H functional organopolysiloxanes of the general formula (III), where e and R have the definition indicated above, f and g are integers, with the proviso that the sum f+g is 66 to 248, preferably 98 to 248, more preferably 118 to 168, that the organopolysiloxanes (2a) contain Si-bonded hydrogen in amounts of 0.011 to 0.044 wt %, preferably of 0.019 to 0.044 wt %, more preferably of 0.022 to 0.032 wt %, and that the number of Si—H groups per molecule in the average composition is greater than 2 and less than 5.

These Si—H-containing polyorganosiloxanes (2a) are preferred especially in combination with unsaturated organopolysiloxane resins (1a) composed of units of the general formula (I), it being known from the prior art, according for example to US2016311980A1 and US20160317427A1, that H-siloxane equilibrates having a relatively low number of Si—H groups exhibit particularly advantageous properties in cosmetic applications.

Si—H-containing organopolysiloxanes (2b) are Si—H functional organopolysiloxanes of the general formula (IV)

$$H_{e'}R_{3-e'}SiO(R^2SiO)_{f'}(RHSiO)_{g'}SiR_{3-e'}H_{e'} \qquad (IV),$$

where e' is 0 or 1, preferably 0,

R has the definition indicated for it above, f' and g' are integers, with the proviso that the sum f'+g' is 8 to 248, preferably 38 to 248, and that the organopolysiloxanes (2b) contain Si-bonded hydrogen in amounts of 0.011 to 0.35 wt %, preferably of 0.045 to 0.156 wt %.

The Si—H-containing organopolysiloxanes (2a) used in the invention preferably have a viscosity of 3 to 15000 mm²/s, very preferably 20 to 10000 mm²/s at 25° C.

The catalyst (K) used in the process of the invention may comprise the same catalysts which it has also been possible to date to use in order to promote the addition of Si-bonded hydrogen onto aliphatic multiple bond. The catalysts preferably comprise a metal from the group of the platinum metals or a compound or a complex from the group of the platinum metals. Examples of such catalysts are metallic and finely divided platinum, which may be located on supports such as silicon dioxide, aluminium oxide or activated carbon, or compounds or complexes of platinum, such as platinum halides, e.g. PtCl$_4$, H$_2$PtCl$_6$·6H$_2$O, Na$_2$PtCl$_4$·4H$_2$O, platinum-olefin complexes, platinum-alcohol complexes, platinum-alkoxide complexes, platinum-ether complexes, platinum-aldehyde complexes, platinum-ketone complexes, including reaction products of H$_2$PtCl$_6$·6H$_2$O and cyclohexanone, platinum-vinyl siloxane complexes, such as platinum-1,3-divinyl-1,1,3,3-tetramethyldisiloxane complexes with or without detectable inorganically bonded halogen therein, bis(□-picoline)platinum dichloride, trimethylenedipyridineplatinum dichloride, dicyclopentadieneplatinum dichloride, dimethylsulfoxideethyleneplatinum(II) dichloride, cyclooctadiene-platinum dichloride, norbornadiene-platinum dichloride, □-picoline-platinum dichloride, cyclopentadiene-platinum dichloride, and also reaction products of platinum tetrachloride with olefin and primary amine or secondary amine or primary and secondary amine, such as the reaction product of a 1-octene solution of platinum tetrachloride with sec.-butylamine, or ammonium-platinum complexes. Preferred hydrosilylation catalysts are platinum compounds which are present in a solvent suitable for use in cosmetic formulations.

The catalyst (K) is preferably in amounts of 1 to 100 ppm by weight (parts by weight per million parts by weight), very preferably 2 to 75 ppm by weight, calculated in each case as elemental platinum and based on the total weight of the unsaturated organopolysiloxane resins (1a), of the unsaturated organopolysiloxanes (1b), optionally of the unsaturated organic components (1c) of the Si—H functional organopolysiloxanes (2a) or of the mixture of the Si—H functional organopolysiloxanes (2a) with (2b) and the diluent (4).

The unsaturated organopolysiloxane resins (1a) preferably have a viscosity of greater than 0.7 mm²/s at 25° C. More preferred organopolysiloxane resins are those having a viscosity of greater than 1000 mm²/s at 25° C., or those which are solids. The weight-average molecular weight M$_w$ determined by gel permeation chromatography (relative to a polystyrene standard) of these organopolysiloxane resins is preferably 334 to 200 000 g/mol, more preferably 1000 to 20 000 g/mol.

The unsaturated organopolysiloxane resins (1a) preferably have an iodine number of less than 254, more preferably an iodine number of less than 76.

Examples of radicals R are alkyl radicals, such as the methyl, ethyl, n-propyl, isopropyl, 1-n-butyl, 2-n-butyl, isobutyl, tert-butyl, n-pentyl, isopentyl, neopentyl, tert-pentyl radical, hexyl radicals, such as the n-hexyl radical, heptyl radicals, such as the n-heptyl radical, octyl radicals, such as the n-octyl radical and isooctyl radicals, such as the 2,2,4-trimethylpentyl radical, nonyl radicals, such as the n-nonyl radical, decyl radicals, such as the n-decyl radical, dodecyl radicals, such as the n-dodecyl radical, and octadecyl radicals, such as the n-octadecyl radical; cycloalkyl radicals, such as cyclopentyl, cyclohexyl, cycloheptyl and methylcyclohexyl radicals; aryl radicals, such as the phenyl, naphthyl, anthryl and phenanthryl radical; alkaryl radicals, such as o-, m- and p-tolyl radicals, xylyl radicals and ethylphenyl radicals; and aralkyl radicals, such as the benzyl radical, the □- and the □-phenylethyl radical.

Examples of substituted radicals R are haloalkyl radicals, such as the 3,3,3-trifluoro-n-propyl radical, the 2,2,2,2',2', 2'-hexafluoroisopropyl radical, the heptafluoroisopropyl radical, and haloaryl radicals, such as the o-, m- and p-chlorophenyl radical.

The radical R is preferably a monovalent hydrocarbon radical having 1 to 6 carbon atoms, the methyl radical being particularly preferred.

The unsaturated hydrocarbon radical R$^1$ is preferably bonded to an M unit (=M$_{Vi}$) or D unit (=D$_{Vi}$), more preferably to an M unit, with the molar ratio M:(M$_{Vi}$+D$_{Vi}$), preferably M:M$_{Vi}$, being preferably in the 0 to 50 range, more preferably in the 0 to 20 range, very preferably in the 2.5 to 13 range.

Examples of radicals R$^1$ are alkenyl radicals, such as the vinyl, 5-hexenyl, cyclohexenyl, 1-propenyl, allyl, 3-butenyl and 4-pentenyl radical, and alkinyl radicals, such as the ethinyl, propargyl and 1-propinyl radical. The radical R$^1$ preferably comprises alkenyl radicals, more preferably □-alkenyl radicals, more particularly the vinyl radical.

The preparation of the hydrophobic gels is easy to carry out. In general all of the constituents apart from the catalyst are introduced and slowly stirred until the solid unsaturated organopolysiloxane resin, if used, has dissolved, or until all of the components have undergone homogeneous mixing, and then the catalyst is added. The composition may be left at room temperature until a gel has formed, or if necessary is heated. Compositions which comprise unsaturated organopolysiloxane resins are heated preferably to a temperature between 50° C. and 130° C., more preferably between 70° C. and 120° C., until the mixture gels or becomes solid. Where appropriate, the same applies to compositions comprising unsaturated organopolysiloxanes having a reactivity comparable with that of unsaturated organopolysiloxane resins. Gelling takes place preferably within ten hours, more preferably within three hours. Organopolysiloxane gels are obtained which are suitable for use in cosmetic formulations.

For the preparation of the hydrophobic organopolysiloxane gels, unsaturated organopolysiloxane resins (1a) or unsaturated organopolysiloxanes (1b) are used in amounts of preferably 4.5 to 0.1 mol, more preferably 2 to 0.3 mol, very preferably 1.8 to 0.5 mol, of hydrocarbon radical with aliphatic C—C multiple bond per mol of Si-bonded hydrogen in the Si—H-containing organopolysiloxanes (2a) and optionally (2b).

The reaction is terminated at the end of the reaction time by the addition preferably of a hydrosilylation catalyst poison as stopper compound (5), with the effect of ending the after-curing brought about by remaining crosslinking hydrosilylation reactions which occur in the silicone elastomers. Stoppers used here are catalyst poisons which irreversibly alter and so deactivate the hydrosilylation catalyst.

The stopper compounds (5) are used preferably in amounts of at least 1.1 mol of stopping functional group, preferably mercapto group, per mol of elemental platinum in the catalyst (K). It has proved here to be particularly advantageous to use a significantly superstochiometric amount of the stopper, since this has a positive effect on the long-term retention of creaminess by the completed gel.

Illustrative of stopper compounds (5), which are suitable for ending the after-curing are sulfur-organic compounds, such as organic compounds containing mercapto groups. Other suitable compounds are stated in U.S. Pat. No. 6,200, 581. Preferred hydrosilylation catalyst poisons as stopper compounds (5) are organopolysiloxanes containing mercaptoalkyl groups, very preferably organopolysiloxanes containing 3-mercaptopropyl groups, such as mercaptopropyl-functional silsesquisiloxanes or mercaptopropyl-functional polyorganosiloxanes.

Organopolysiloxanes containing mercaptoalkyl groups and used as stopper compounds (5) are used preferably in amounts of 200 to 1.1 mol, more preferably 50 to 1.5 mol, very preferably to 2.0 mol of mercapto groups per mol of elemental platinum in the catalyst (K).

Depending on the process selected, in a second or third optional process step there may optionally be dilution of the hydrophobic organopolysiloxane-based gel initially obtained.

In the optional step of diluting the hydrophobic organopolysiloxane-based gel it is possible to prepare a multiplicity of different hydrophobic gels, which vary in a broad range in their consistency and their profile of properties. It is possible here to use the same diluent (4) as used in the first, or first two, process step(s), or a second diluent (4) different from this.

Compound (3)

The organopolysiloxanes (3a) containing glycoside radicals are those of the formula (V)

$$R_h R^3{}_i SiO_{(4-h-i)/2} \qquad (V),$$

where

R may have the definitions indicated above, $R^3$ may be identical or different and is a radical of the formula $$Z—(R_4O)_j—R^5— \qquad (Va), \text{ in which}$$

Z is a glycoside radical composed of 1 to 10 monosaccharide units, preferably glucose units, $R^4$ may be identical or different and is a divalent hydrocarbon radical having 2 to 4 carbon atoms, j is 0 or an integer from 1 to 20, and $R^5$ may be identical or different and is a divalent hydrocarbon radical having 2 to 12 carbon atoms, h and i are each 0, 1, 2 or 3, with the proviso that $h+i \leq 3$ and in at least one repeating unit i has a value of at least 1.

Examples of radicals of the formula (Va) are $$G\text{-}(CH_2CH_2O)—CH_2CH_2—,$$

$$G\text{-}(CH_2CH_2O)—CH_2CH_2CH_2—,$$

$$G_2\text{-}(CH_2CH_2O)—CH_2CH_2—,$$

$$G_2\text{-}(CH_2CH_2O)—CH_2CH_2CH_2—,$$

where G is a glycoside radical of the formula $(C_6H_{11}O_6)—$ and $G_2$ is a glycoside radical composed of two glucose units.

Preferred examples of radicals of the formula (Va) are $$G\text{-}(CH_2CH_2O)—CH_2CH_2CH_2— \text{ and } G_2\text{-} (CH_2CH_2O)—CH_2CH_2CH_2—,$$

where G and $G_2$ have the definition indicated for them above.

Preferred polyorganosiloxanes of the formula (V) containing glucoside radicals are those which have an HLB of 3 to 18, particularly of 4 to 16, more particularly of 4 to 12; HLB values from 5 to 10 have proven especially advantageous.

The organopolysiloxanes (3b) containing polyglycol radicals are those of the formula (VI)

$$R_h R^6{}_i SiO_{(4-h-i)/2} \qquad (VI),$$

where

R may have the definitions indicated above, $R^6$ may be identical or different and is a radical of the formula $$P—R^7—R^8— \qquad (VIa), \text{ in which}$$

P is a polyoxyalkylated radical of the type $—(OC_nH_{2n})_m—OH,$ $R^7$ is a chemical bond or a divalent hydrocarbon radical having 1 to 10 carbon atoms, preferably a radical of the formula $—CH_2—$, $—CH(CH_3)—$ or $—C(CH_3)_2—$, more preferably a radical of the formula $—CH_2—$, and n is an integer from 1 to 4, preferably 2 or 3, and m is a positive integer, preferably from 1 to 40, $R^8$ is a divalent hydrocarbon radical having 2 to 12 carbon atoms, preferably a radical of the formula $-CH_2-CH_2-$,
$-CH_2-CH(CH_3)-$ or $-CH_2-C(CH_3)_2-$, more preferably a radical of the formula $-CH_2-CH_2-$, h and i each have the definition indicated earlier on above.

Preferred polyorganosiloxanes of the formula (VI) containing polyglycol radicals are those which have an HLB of 3 to 18, particularly of 4 to 16, more particularly of 4 to 12; HLB values from 5 to 10 have proven especially advantageous.

Preferred examples of polyoxyalkylated radicals P are those of the general formula $$-(OCH_2CH_2)_o[OCH_2CH(CH_3)]_p-OH \qquad (VIb),$$

where
o is 0 or an integer from 1 to 30, preferably 2 to 20, more preferably 6 to 14, and
p is 0 or an integer from 1 to 30, preferably 0 to 10, more preferably 0,
where the sum of o+p is 1 to 40, preferably 2 to 20, more preferably 6-14.

A particularly preferred example of a polyoxyalkylated radical P is the polyethylene glycol radical having about 10 oxyethylene units.

The formula (VIb) is to be understood such that o $-(OCH_2CH_2)-$ groups and p $-[OCH_2CH(CH_3)]-$ groups may be distributed in any way in the radical P.

The organopolysiloxanes (3c) containing cyclodextrin radicals are those of the formula (VII)

$$R_hR^9{}_iSiO_{(4-h-i)/2} \qquad (VII),$$

where
R may have the definitions indicated above,
$R^9$ may be identical or different and is a radical of the formula $$C-R^{10}- \qquad (VIIa), \text{ in which}$$

C is a cyclodextrin radical of the form

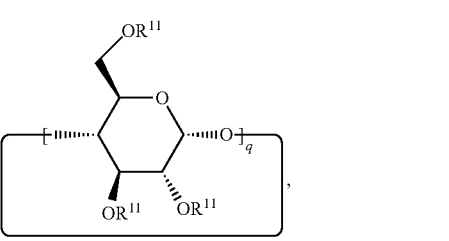

in which $R^{11}$ is a hydrogen radical or a methyl radical, and
q is the integers 6 (alpha cyclodextrin), 7 (beta cyclodextrin) or 8 (gamma cyclodextrin),
$R^{10}$ is a divalent hydrocarbon radical having 2 to 18 carbon atoms which is optionally interrupted with heteroatoms,
h and i each have the definition indicated earlier on above.

Non-limiting examples of radicals $R^{10}$ are radicals of the form $-CH_2-CH_2-$, $-CH_2-CH(CH_3)-$ or $-CH_2-C(CH_3)_2-$, $-CH_2CH_2CH_2-$, $-CH_2(CH_2)_2CH_2-$, $-CH_2(CH_2)_3CH_2-$, $-CH_2(CH_2)_4CH_2-$, $-CH_2(CH_2)_6CH_2-$, $-CH_2(CH_2)_{10}CH_2-$, $-CH_2-CH(CH_3)_2CH_2-$, more preferably the radicals $-CH_2(CH_2)_6CH_2-$ and $-CH_2(CH_2)_{10}CH_2-$.

Preferred polyorganosiloxanes of the formula (VII) containing cyclodextrin radicals are those which have an HLB of 3 to 18, particularly of 4 to 16, more particularly of 4 to 12; HLB values from 5 to 10 have proven especially advantageous.

The organopolysiloxanes (V) containing a glycoside radical, the organopolysiloxanes (VI) containing a polyoxyalkylene radical and the organopolysiloxanes (VII) containing a cyclodextrin radical are prepared by reaction of an organosilicon compound containing Si—H functions and of the formula $$R_hH_iSiO_{(4-h-i)/2} \qquad (IX),$$

in which R, h and i have the definitions stated above and in which at least in one repeating unit i has a value of at least 1,
with unsaturated compounds of the formula $$Z-(R_4O)_j-R^{12} \qquad (Vb),$$

in which Z, $R^4$ and j have the definitions stated above and $R^{12}$ is a monovalent hydrocarbon radical having 2 to 12 carbon atoms, onto which Si—H groups may be added in a hydrosilylation reaction; preferably a monovalent hydrocarbon radical having 3 to 17 carbon atoms, preferably 4 to 16 carbon atoms and containing a terminal aliphatic C—C multiple bond, and very preferably an allyl radical,
and/or with unsaturated compounds of the formula $$P-R^7-R^{13} \qquad (VIb)$$

where P and $R^7$ have the definitions indicated above and $R^{13}$ is a monovalent hydrocarbon radical having 2 to 12 carbon atoms, onto which Si—H groups may be added in a hydrosilylation reaction; preferably a monovalent hydrocarbon radical having 2 to 12 carbon atoms, preferably 3 to 12 carbon atoms and containing a terminal aliphatic C—C multiple bond, and very preferably a vinyl radical or an allyl radical, and/or with an unsaturated compound of the formula $$C-R^{14} \qquad (VIIb)$$

in which C has the definitions indicated above and $R^{14}$ is a monovalent hydrocarbon radical having 2 to 18 carbon atoms, onto which Si—H groups may be added in a hydrosilylation reaction; preferably a monovalent hydrocarbon radical having 3 to 17 carbon atoms, preferably 4 to 16 carbon atoms and containing a terminal aliphatic C—C multiple bond, and very preferably an octenyl radical or a dodecenyl radical.

In one preferred embodiment of the invention the organosilicon compounds of the formula (IX) are Si—H-containing polyorganosiloxanes of the general formula $$H_eR_{3-e}SiO(R_2SiO)_f(RHSiO)_gSiR_{3-e}H_e \qquad (III),$$

which has already been described earlier on above, where the composition of the organopolysiloxanes of the formula (III) for preparing the organopolysiloxanes of the formulae (V), (VI) and (VII) is independent of the composition of the organopolysiloxanes of the formula (III) for preparing the hydrophobic organopolysiloxane gels. In particular the two organopolysiloxanes of the formula (III) for the various end uses may be different from one another and in general are different as well.

The resulting structures of the organopolysiloxanes of the formulae (V), (VI) and (VII) are obvious to the skilled person from the information given here.

Particularly preferred unsaturated compounds (Vb) are alkenylglucosides (Vc), more preferably the (2-allyloxy-ethoxy)glucoside of the formula This alkenylglucoside is prepared by the process described in U.S. Pat. No. 5,831,080 in example 1 (A) (column 8, lines 23-43), with the difference that in the last step the solvent is not distilled off completely, since that would lead to a material which was glasslike at room temperature; instead, a solvent switch to 1,2-propanediol is performed. The product is an approximately 50% solution of the alkenylglucoside in 1,2-propanediol. The alkenylglucoside is partly in condensed form as an oligoglucoside.

The compounds (Vc) are therefore preferably used as solutions in an organic solvent. Examples of organic solvents are alcohols, such as glycerol, 1,2-propanediol, methanol, ethanol, n-propanol and isopropanol; saturated hydrocarbons, such as n-pentane, n-hexane, n-heptane and n-octane, and branched isomers thereof, such as isododecane; mineral spirits, e.g. alkane mixtures having a boiling range of 80° C. to 140° C. at 1020 hPa; unsaturated hydrocarbons such as 1-hexene, 1-heptene, 1-octene and 1-decene; aromatic hydrocarbons such as benzene, toluene and xylenes; halogenated alkanes having 1 to 6 carbon atom(s), such as methylene chloride, trichloroethylene and perchloroethylene; ethers, such as di-n-butyl ether; esters, such as ethyl acetate, isopropyl palmitate and isopropyl myristate (i.e. isopropylester of myristic acid); and ketones, such as methyl ethyl ketone and cyclohexanone.

The mixture (X) contains 0.1 to 20 wt % of the compound (3), preferably 0.2 to 15 wt %, more preferably 0.3 to 10 wt %.

Diluents (4)

Diluents (4) are different from (3a), (3b) and (3c). They are preferably organopolysiloxanes having 2 to 200 Si atoms, more preferably organopolysiloxanes having 2 to 50 Si atoms, very preferably linear organopolysiloxanes having a viscosity of 1.5 to 50 mm$^2$/s at 25° C., or organic diluents, or mixtures of organopolysiloxanes having 2 to 200 Si atoms with organic diluents.

100 wt % of the hydrophilic organopolysiloxane gel preparation of the invention contains 20 to 98 wt % of diluents (4), preferably 30 to 98 wt %, more preferably 50 to 90 wt %, very preferably 60 to 85 wt %, and 2 to 80 wt %, preferably 2 to 70 wt %, more preferably 10 to 50 wt %, very preferably 15 to 40 wt %, of the mixture (X).

Unreactive or relatively unreactive diluents (4) are preferred. In the context of the present invention, the term "unreactive" is used in relation to the crosslinking reaction in question and to the reactants employed herein. A relatively unreactive diluent (4) is less than one tenth as reactive with the reactants of the crosslinking reaction by comparison with the reactants with one another in the crosslinking reaction.

Suitable examples of diluent (4) include cyclic and linear organopolysiloxanes, organic diluents, or mixtures of organopolysiloxanes and organic diluents.

The organopolysiloxane may be a single organopolysiloxane or a mixture of organopolysiloxanes. The organopolysiloxane may carry alkyl, aryl, alkaryl and aralkyl groups. Such organopolysiloxanes may be indicated illustratively by polydimethylsiloxane, polydiethylsiloxane, polymethylethylsiloxane, polymethylphenylsiloxane and polydiphenylsiloxane, but are not limited to these.

Cyclic polydimethylsiloxanes may be indicated illustratively by hexamethylcyclotrisiloxane, octamethylcyclotetrasiloxane, decamethylcyclopentasiloxane and dodecamethylcyclohexasiloxane, but are not limited to these.

Also possible is the use of functional organopolysiloxanes as diluents (4), examples being acrylamide-functional siloxane fluids, acryloyl-functional siloxane fluids, amide-functional siloxane fluids, amino-functional siloxane fluids, carbinol-functional siloxane fluids, carboxy-functional siloxane fluids, chloroalkyl-functional siloxane fluids, epoxy-functional siloxane fluids, glycol-functional siloxane fluids, ketal-functional siloxane fluids, mercapto-functional siloxane fluids, methyl ester-functional siloxane fluids, perfluoro-functional siloxane fluids and silanol-functional siloxanes.

The organopolysiloxane is preferably a polydimethylsiloxane having 2 to 200 Si atoms, more preferably 2 to 50 Si atoms; particularly preferred are linear polydimethylsiloxanes having a viscosity of 1.5 to 50 mm$^2$/s at 25° C.

Organic diluents (4) used may be aliphatic hydrocarbons, such as, for example, pentane, cyclohexane, heptane, paint benzines, fatty oils, including polyunsaturated □-3- and □-6-fatty acids and their esters; vegetable oils, such as peanut, olive, palm, canola, maize kernel, soya and sunflower oil and the like; and natural and synthetic oils or oil-soluble solids, such as various mono-, di- and triglycerides, polyoxyalkylated vegetable oils, lanolin, lecithin and the like; and petroleum hydrocarbons, such as petrolatum, mineral oil, benzine, petroleum ether. These examples serve for illustration and should not be understood as any limitation. The organic diluent (4) may also comprise aliphatic or alicyclic hydrocarbons having 4 to 30 carbon atoms, preferably saturated hydrocarbons. The aliphatic hydrocarbons may be straight-chain or branched, and the alicyclic hydrocarbons may be unsubstituted cyclic hydrocarbons or aliphatic hydrocarbon-substituted hydrocarbons. Examples of suitable hydrocarbons are n-heptane, n-octane, isooctane, n-decane, isodecane, n-dodecane, isododecane, cyclohexane, cycloheptane, cyclooctane, methylcyclohexane, dimethylcyclohexane, ethylcyclohexane, nonylcyclohexane and the like. This enumeration as well serves for illustration and should not be understood as any limitation.

Other suitable organic diluents (4) are volatile flavouring substances, such as peppermint oil, spearmint oil, menthol, vanilla, cinnamon oil, clove oil, bay oil, anise oil, eucalyptus oil, thyme oil, cedar oil, nutmeg oil, sage oil, cassia oil, cocoa, liquorice juice, starch sugar syrup from corn with high fructose content, citrus oils, such as lemon, orange, lime and grapefruit, fruit essences, such as apple, pear, peach, grape, strawberry, raspberry, cherry, plum, pineapple and apricot; and other useful flavouring substances, including aldehydes and esters, such as ethyl cinnamate, cinnamaldehyde, eugenyl formate, p-methylanisol, acetaldehyde, benzaldehyde, anisaldehyde, citral, neral, decanal, vanillin, tolylaldehyde, 2,6-dimethyloctanal and 2-ethylbutyraldehyde.

A part or the entire organic diluent (4) may comprise one or more volatile fragrances, such as natural products and perfume oils. A number of representative natural products and perfume oils are amber, bezoin, civet, clove, cedar oil, jasmine, mate, mimosa, musk, myrrh, iris, sandalwood oil and vetiver oil; aroma chemicals, such as amyl salicylate, amylcinnamaldehyde, benzyl acetate, citronellol, coumarin, geraniol, isobornyl acetate, ambrette and terpinyl acetate, and various classic perfume oil families, such as the floral bouquet family, the oriental family, the chypre family, the wood family, the citrus family, the canoe family, the leather family, the spice family and the herb family.

Preferred organic diluents (4) have a viscosity in the range from 0.5 to 200 mm²/s (25° C.), with particular preference being given to those diluents having a boiling point in the range from 50° C. to 300° C.

Numerous mixtures of diluent (4) may be used, and are confined only to those compositions in which no phase separation occurs following the production of the hydrophilic organopolysiloxane gel preparation of the invention.

The hydrophilic organopolysiloxane gel preparations of the invention have an excellent skin feel.

Active Ingredient for Body Care or Health Care

A further subject of the present invention, therefore, are cosmetic preparations or preparations for body care and health care, washing and cleaning preparations, preparations for long-lasting fragrancing or insect repellency, such preparations comprising the hydrophilic organopolysiloxane gel preparations of the invention. They further comprise adjuvants widely known in this field, and also, for example, "active ingredients for body care or health care". In the present context, this means any compound or mixture of compounds which are known to the skilled person in the art as additives to body care formulations and which are typically added in order to treat the hair or the skin, in order to achieve a cosmetic and/or aesthetic benefit; any compound or mixture of compounds which are known in the art to achieve a pharmaceutical or medical benefit; any compound with which a pharmacological efficacy or other effect in diagnosis, healing, alleviation, treatment or prevention of diseases is to be achieved, or in order to influence the structure or any function of the human or animal body; and any compound which can undergo a chemical change in the production of medicament products and can be present in modified form in medicaments in order to bring about the specified efficacy or the specified effect.

The active ingredients for body care or health care are preferably selected from the group of fat-soluble or oil-soluble vitamins, oil-soluble medicaments, including anti-acne agents, antibacterial agents, fungicidal agents, anti-inflammatory agents, dandruff control agents, narcotics, pruritus-relieving agents, skin inflammation inhibitors and agents which are generally considered to be barrier films, and oil-soluble UV absorbers.

Examples of useful active constituents for use in the optional third process step according to the invention are as follows:

Nonlimiting examples of oil-soluble vitamins are vitamin A₁, RETINOL, C₂ to C₁₈ esters of RETINOL, vitamin E, TOCOPHEROL, esters of vitamin E and mixtures thereof. RETINOL embraces trans-RETINOL, 13-cis-RETINOL, 11-cis-RETINOL, 9-cis-RETINOL and 3,4-didehydro-RETINOL.

It should be noted that RETINOL is an International Nomenclature Cosmetic Ingredient (INCI) name, confirmed by The Cosmetic, Toiletry and Fragrance Association (CTFA), Washington DC, for vitamin A. Other suitable vitamins and the INCI names for the vitamins in question which are included herein are RETINYL ACETATE, RETINYL PALMITATE, RETINYL PROPIONATE, a-TOCOPHEROL, TOCOPHERSOLAN, TOCOPHERYL ACETATE, TOCOPHERYL LINOLEATE, TOCOPHERYL NICOTINATE and TOCOPHERYL SUCCINATE.

Some examples of commercially available products which are suitable for use herein are vitamin A acetate from Fluka Chemie AG, Buchs, Switzerland; CIOVI-OX T-50, a vitamin E product from Henkel Corporation, La Grange, Illinois; COVI-OX T-70, another vitamin E product from Henkel Corporation, La Grange, Illinois, and vitamin E acetate, a product from Roche Vitamins & Fine Chemicals, Nutley, New Jersey.

Representative examples of some suitable oil-soluble medicaments which can be added as active constituents are clonidine, scopolamine, propranolol, estradiol, phenylpropanolamine hydrochloride, ouabain, atropin, haloperidol, isosorbide, nitroglycerin, ibuprofen, ubiquinone, indomethacin, prostaglandins, naproxen, salbutamol, guanabenz, labetalol, pheniramine, metrifonate and steroids.

Likewise encompassed herein as a medicament for the purposes of the present invention are anti-acne agents, such as benzoyl peroxide, triclosan and tretinoin; antibacterial agents such as chlorhexidine gluconate; fungicidal agents, such as miconazole nitrate; anti-inflammatory agents, such as salicylic acid; corticosteroidal medicaments; non-steroidal anti-inflammatory agents, such as diclofenac; dandruff control agents, such as clobetasol propionate and retinoids, narcotics, such as lidocaine; pruritus-relieving agents, such as polidocanol; skin inflammation inhibitors, such as prednisolone, and agents which are generally regarded as barrier films.

Representative examples of oil-soluble UV absorbers which may be added as active constituents are 1-(4-methoxyphenyl)-3-(4-tert-butylphenyl)propane-1,3-dione (INCI: Butyl Methoxydibenzoylmethane), 2-Ethylhexyl-(2E)-3-(4-methoxyphenyl)prop-2-enoate (INCI: Octyl Methoxycinnamate), 4-Hydroxy-2-methoxy-5-(oxo-phenyl-methyl)benzenesulfonic acid (INCI: Benzophenone-4), 2-Hydroxy-4-methoxybenzophenon-5-sulfonic acid sodium salt (INCI: Benzophenone-5) and 2-Ethylhexyl-2-hydroxy-benzoate (INCI: Ethylhexyl Salicylate).

A Further Subject is the Process for Producing the Hydrophilic Organopolysiloxane Gel Preparation of the Invention For this purpose the components are combined with one another.

The production process here corresponds exactly or substantially to the production process for the hydrophobic elastomer gels. The hydrophobic elastomer gels are generally produced in a single-stage process. In exceptional cases, there is also a two-stage procedure known wherein two different unsaturated compounds, generally with different reactivity, undergo a staged reaction with Si—H-functional organopolysiloxanes.

Where the production process includes a step for viscosity adjustment by addition of a diluent after the end of hydrosilylation reaction, the compound (3) may be added in this step. In the absence of such a step in the process of producing the hydrophobic organopolysiloxane gel, the compound (3) is added in a separate metering step.

It is therefore a major advantage that there is no need for separate production of the hydrophilic elastomer gels in a single-stage or preferably two-stage process.

Accordingly, a single operation yields two significantly different products with a minimum adaptation to the process.

It is especially advantageous here that the compounds (3), as is apparent from the known prior art, are themselves produced and used anyway for other purposes, or else can be used for other purposes, as emulsifiers, foam stabilizers, formulating assistants or the like, and are so used, and are therefore readily obtainable commercially.

It is also distinctive for the simplicity of the process of the invention that the switch of property from a hydrophobic to a hydrophilic gel works with all those silicone-based, hydrophobic elastomer gel technologies that are of practical relevance and are found in the prior art.

A hydrophobic organopolysiloxane gel becomes a hydrophilic organopolysiloxane gel of the invention by the admixing, after the addition of the stopper compound, of a compound (3). This may be accomplished by metering the compound (3) together with the diluent in the optional dilution step in producing the hydrophobic organopolysiloxane gel, or, if there is no dilution step after the addition of the stopper compound, by adding the compound (3) in a separate metering step.

Use is made here of prior-art high-shear mixing technologies of the kind that would also be used in the context of the optional dilution step.

Dilution and mixing may take place by intensive mixing and dispersing using suitable stirring assemblies or in rotor-stator stirring apparatuses, colloid mills, high-pressure homogenizers, microchannels, membranes, jet nozzles and the like, or by means of ultrasound. Homogenizing equipment and methods employed in these contexts are in accordance with the prior art. Homogenizing equipment and methods are described for example in Ullmann's Encyclopedia of Industrial Chemistry, CD-ROM edition 2003, Wiley-VCH Verlag, under the heading "Emulsions".

For the production it is essential that as a result of the addition of the compound (3), which itself does not have a creamy-gel consistency, the viscosity of the resultant hydrophilic organopolysiloxane gel preparation of the invention is lower by comparison with production without a hydrophilic component. If the same viscosity level is desired as for the hydrophobic organopolysiloxane, then a correspondingly lower amount of diluent (4) can be used. The particular reduction in diluent (4) required must be ascertained experimentally and is dependent on the particular hydrophilic component. Consequently, the result is not the same if, for example, a formulator mixes the hydrophobic and hydrophilic components with one another. The viscosity resulting from this procedure does not correspond to the viscosity of the hydrophobic organopolysiloxane gel in its original supply form. In particular, therefore, when drawing up recipes of cosmetic preparations, the same result is not obtained. It is known that the viscosity of the elastomer gels has an influence on the skin feel which they cause.

A key advantage of the hydrophilic organopolysiloxane gel preparations of the invention is their improved compatibility with polar or hydrophilic organic substances, glycerol for example, and even water. These important cosmetics ingredients are immiscible, or miscible only in very small amounts, with conventional organopolysiloxane gels. The hydrophilic organopolysiloxane gel preparations of the invention are capable of absorbing highly polar compounds such as water or glycerol while retaining the viscous gel structure and forming a single-phase, homogeneous mixture.

By virtue of their improved compatibility with polar and hydrophilic organic substances and even water, the hydrophilic organopolysiloxane gel preparations of the invention exhibit a thickening effect even in water-based or alcohol-based formulations, and endow such formulations with a preferred silky skin feel.

Relative to the prior art, the hydrophilic organopolysiloxane gel preparations of the invention not only have the advantage that the cost and complexity involved in drawing up a comprehensive portfolio are considerably reduced, but also have technical advantages. Relative to hydrophilic organopolysiloxane gels of US2016311980A1, it has been found that the hydrophilic organopolysiloxane gel preparations that are subject of the present invention, for comparable composition and water absorption capacity, can be produced transparently and have a better skin feel than comparable gels of US2016311980A1. An example of this is given in the experimental section. A transparent organopolysiloxane gel here is able to cover a larger application spectrum, since it may be used both in transparent and in opaque formulations without disrupting the appearance of the final formulation.

The hydrophilic organopolysiloxane gel preparations of the invention differ from hydrophilic preparations obtained from a hydrophobic gel by incorporation of a hydrophilic, silicone-free organic component into a hydrophobic organopolysiloxane gel. The hydrophilic organopolysiloxane gel preparations of the invention may be obtained transparently, as they consist of components which are miscible and compatible with one another. This is not the case with preparations made up of organic hydrophilic and hydrophobic organopolysiloxane gels. The latter preparations, because of the incompatibility of their components, are cloudy and tend to separate from one another again in the presence of water, so that the organic component acts, for example, as an emulsifier for the silicone component, but in no way supports or boosts the performance features of that component. The hydrophilic organopolysiloxane gel preparations of the invention display this behaviour—that is, it has been found that the performance features of the hydrophobic organopolysiloxane gels could be improved through the admixing of the hydrophilic component (3). At the same time, the components of the hydrophilic organopolysiloxane gel preparations of the invention remain homogeneously united and do not separate into the individual constituents, which then subsequently, independently of one another, exert a possibly different function.

The hydrophilic organopolysiloxane gel preparation of the invention is preferably homogenized to a creamy consistency using standard high-shear mixing technologies. Technologies suitable for this purpose are the same as those stated in this text for the optional dilution step and the addition of the compound (3).

"Creamy" in relation to the organopolysiloxane gel preparation means that the initial gel has been sheared to a creamy consistency. The resulting creamy organopolysiloxane gel preparation may, according to its nature, be pourable or relatively stiff. The attribute "creamy" distinguishes these sheared gels, which can be transparent or opaque, from the gels produced directly by gelation of the reactive constituents.

"Storage-stable" in the context of this invention is understood to mean that the hydrophilic organopolysiloxane gel preparations formed do not separate into two or more phases within 6 months of storage at room temperature. Within this period there is preferably no change in the softness of the gel.

The skilled person is able to understand that the absorption capacity for diluent (4) is generally limited because of the three-dimensional network structure of organopolysiloxane gels, and may vary depending on the network structure and network composition. If the absorption capacity for diluent (4) is exceeded, the formation of a diluent phase is apparent alongside a gel phase. In this connection, the component (3) also displays a certain diluent effect, as it does not possess any highly viscous gel structure in itself. With similar simplicity to the use of the diluents (4), the use of the component (3) is incorporated into the existing production process of the hydrophobic organopolysiloxane gels employed as starting product.

A further subject of the invention is the use of the hydrophilic organopolysiloxane gel preparation of the invention in cosmetic preparations or preparations for body care and health care or in washing and cleaning products or in products for long-lasting fragrancing or insect repellency.

The hydrophilic organopolysiloxane gel preparations of the invention are suitable with particular preference for cosmetic applications, and are therefore preferably employed in cosmetic compositions. They are also suitable, however, for other applications, for example for medical and industrial applications.

They are capable, surprisingly, of absorbing water into the gel structure, without the preparation being split into its constituents. Accordingly, the physical mixture unexpectedly behaves like a homogeneous substance composed of only one species. The capacity to absorb water into the gel structure improves the compatibility of the hydrophilic organopolysiloxane gel preparations of the invention with aqueous cosmetic preparations and makes them easier to incorporate. In contrast to standard commercial products comprising preparations composed of organopolysiloxane gels and organic emulsifiers, the hydrophilic organopolysiloxane gel preparations of the invention contain only silicone components and so are able to combine the aesthetic skin feel, without reductions in performance capacity, with the advantages of improved compatibility.

The hydrophilic organopolysiloxane gel preparations of the invention are of particular value in body care products. They can be gently distributed on the skin and can therefore be used alone or mixed with other body care product constituents, to form a host of body care products.

Examples of body care product constituents are esters, waxes, oils and fats of animal or plant origin, fatty alcohols, fatty acids, alkyl esters of fatty acids, hydrocarbons and hydrocarbon waxes, water, organic solvents, perfumes, surfactants, oil-soluble vitamins, water-soluble vitamins, oil-soluble medicaments, water-soluble medicaments, UV absorbers and active pharmaceutical compounds.

The hydrophilic organopolysiloxane gel preparations of the invention are suitable more particularly in antiperspirants and deoperspirants, as they leave a dry sensation and do not cool the skin as they evaporate. They are glidable and improve the properties of skin creams, skin care lotions, moisturizers, face treatments, for example acne removers or wrinkle removers, body and face cleansers, bath oils, perfumes, eau de Cologne, sachets, sunscreens, preshave and aftershave lotions, liquid soaps, shaving soaps and shaving foams. They can be used in hair shampoos, hair conditioners, hairsprays, mousses, permanent wave compositions, hair removers and cuticle barriers, to improve shine and dry gliding and to provide conditioning advantages.

In cosmetics they function as distributing agents for pigments in makeup, colour cosmetics, foundation, rouge, lipsticks, lip balm, eyeliner, mascara, grease removers and colour cosmetic removers. They are suitable as administration systems for oil-soluble active constituents stated illustratively herein, such as, for example, vitamins, medicaments and UV absorbers. When used in sticks, gels, lotions, creams and roll-ons, the elastomers impart a dry, silky-smooth feel. When incorporated into cosmetics and other skin care products, the hydrophilic organopolysiloxane gel preparations of the invention impart a matt effect. In addition, the hydrophilic organopolysiloxane gel preparations of the invention exhibit a multiplicity of advantageous properties, such as, for example, clarity, storage stability and simplicity of production. As a consequence of this they have a broad application range, particularly in antiperspirants, deodorants, skin care products, in perfumes as vehicles, and for hair conditioning, for example in hair balm or hair mask conditioners.

The hydrophilic organopolysiloxane gel preparations of the invention have use beyond the body care sector, including their use as a filler or insulating material for electrical cables, soil barriers or water barriers for soil stabilization, or as substitute for epoxy materials which are used in components in the electronics industry. They are likewise suitable as carriers for crosslinked silicone rubber particles. In these applications, they (i) allow simplicity of introduction of particles into such silicone phases or organic phases, such as sealants, paints, coatings, greases, adhesives, antifoams and casting resin compounds, and (ii) provide modified rheological, physical or energy-absorbing properties of such phases, either in their pure state or in their final state.

The hydrophilic organopolysiloxane gel preparations of the invention are additionally capable of acting as carriers for pharmaceuticals, biocides, herbicides, pesticides and other biologically active substances.

In addition, the hydrophilic organopolysiloxane gel preparations of the invention find application as additives for nonwoven cellulose-based carrier substrates or nonwoven synthetic carrier substrates which are used in moist cleansing tissues such as moist tissues, moist paper towels and moist hand towels, which are generally marketed for personal hygiene and domestic cleaning purposes.

The hydrophilic organopolysiloxane gel preparations of the invention can be used as carriers for controlled and easily regulated release of a volatile active organic substance into the free atmosphere when they are mixed with it. The volatile substance may more particularly be a perfume or an insecticide or a substance that repels insects.

In this use, the hydrophilic organopolysiloxane gel preparations of the invention find broad application, for example in the finishing of fibres, textiles and fabrics made of cotton or synthetic fibres, woven fabrics, towels, including paper towels, toilet paper or wiping paper, such as serviettes or kitchen roll, or nonwoven fabric, for long-lasting, controlled fragrancing or insect repellency. The mixture of the hydrophilic organopolysiloxane gel preparation of the invention and the volatile active organic substance may also be applied to fabrics and textiles in washing machines and laundry driers, directly as such or as an addition to detergents and fabric softeners.

The use of the hydrophilic organopolysiloxane gel preparation of the invention as a carrier for controlled and easily regulated release of a volatile active organic substance is employed in particular in the above-stated cosmetic applications, where they may bring about an extra effect to the effect described there, by providing, for example, for controlled delivery of a perfume. The hydrophilic organopolysiloxane gel preparations of the invention may also be used in insect repellent products, where they release an insecticide or a substance that repels insects. Such products may be applied, for example, directly to the skin or to the clothing.

In a further application, the mixture of the hydrophilic organopolysiloxane gel preparation of the invention and the volatile active organic substance may be used for controlled fragrancing or insect repellency in enclosed spaces, such as for example in living spaces, commercial spaces, WCs or vehicles, such as buses and cars.

EXAMPLES

The examples which follow serve for further illustration of the invention and for description of its function and practical application. In this sense they should be understood as being illustrative, not restrictive.

The examples indicate physical parameters that have been determined by the measurement methods described below. In the absence of details in the example text as to the exact traceability of a measurement, such details are already given in the descriptions of the measurement methods that follow here. In this case, in other words, further details are considered to be those given in the texts relating to the measurement methods.

In the text below, Me denotes a methyl radical —$CH_3$.

Analytical Methods:

The viscosity of organopolysiloxane gels/organopolysiloxane gel preparation was determined according to DIN EN ISO 3219 at a shear rate of 1/s and 25° C.

The viscosity of the organopolysiloxanes, such as Si—H-containing crosslinkers, organopolysiloxane resins and polydimethylsiloxanes, was determined according to DIN 53019 in the linear range at 25° C.

The iodine number was determined according to DIN 53241-1 in accordance with the Wijs method.

Gel permeation chromatography for determining the weight-average molecular weight Mw was conducted according to ISO 16014-1 and ISO 16014-3.

In cosmetic applications, the organopolysiloxane gel preparations that are the subject of the invention produce sensorial advantages by improving the spreadability of the product on the skin and giving the product a silky smooth feel. The organopolysiloxane gels are comparable in their performance capacity only when they are adjusted to a uniform viscosity for sensory testing. A viscosity which has proven to be particularly advantageous for this purpose is situated in the range of 75000-120000 mPas at 25° C. One criterion for the successful production of the organopolysiloxane gels, therefore, is the possibility of establishing this viscosity corridor. If this is not possible, there is no comparability with the other organopolysiloxane gels.

The sensorial properties of the organopolysiloxane gels described in the examples below were assessed by a trained group of 5 testers (panellists).

The panellists applied 0.05 g of each product to the cleaned lower arm over a circular area of 20 $cm^2$, and the organopolysiloxane gels were compared for their spreadability relative to one another. Application was made with the index finger or middle finger and with a rotational speed of two revolutions per second. A total of 30 revolutions were conducted. After a waiting time of 60 seconds, the residues of the organopolysiloxane gels were compared for their silkiness relative to one another.

Relative direct comparability is always possessed here solely by the organopolysiloxane gels that have been produced using the same or at least an equivalent diluent (4), i.e. more particularly with a volatile or nonvolatile diluent. Since different diluents (4) result in different behaviour on application and in terms of residue, products having different diluents (4) must be evaluated separately from one another in each case.

Example 1 (Inventive)

A 2000 ml glass reaction vessel is fitted with a condenser with attached nitrogen inlet, heating mantle, anchor stirrer and temperature control. The reaction vessel is charged with 515 g of a linear trimethylsilyl-terminated polydimethylsiloxane having a viscosity of 5 mPas at 25° C.

Thereafter 80 g of an Si—H-containing polydimethylsiloxane of the formula $(Me_3SiO_{1/2})(Me_2SiO_{2/2})_a$ $(MeHSiO_{2/2})_b(Me_3SiO_{1/2})$ are added, with a:b=55:1 and a chain length of a+b=134 repeating units, and 20 g of an Si—H-containing polydimethylsiloxane $(Me_3SiO_{1/2})$ $(Me_2SiO_{2/2})_a(MeHSiO_{2/2})_b(Me_3SiO_{1/2})$ are added with a:b=50:1 and a chain length of 450 including the terminal units.

Then 107.5 g of a 50% solution of an MQ resin ($M/M^{Vi}/Q$=7.6/1/11.4; $M_w$=2570, $M_n$=5440, iodine number=18; M=$Me_3SiO_{1/2}$, $M^{Vi}$=$Me_2ViSiO_{1/2}$, Q=$SiO_{4/2}$ with Me=methyl radical and Vi=vinyl radical) in the same linear trimethylsilyl-terminated polydimethylsiloxane having a viscosity of 5 mPas at 25° C., which is also used as diluent, are added. Lastly 0.7 g of a mixture of platinum-1,3-divinyl-1,1,3,3-tetramethyldisiloxane complex in divinyltetramethyldisiloxane is added, the mixture being adjusted such that the amount added corresponds to 52 ppm by weight of Pt, based on the sum total of the mass of the MQ resin and of the two Si—H-containing organopolysiloxanes. The reaction vessel is closed and purged with nitrogen for 5 min.

The reaction mixture is subsequently heated to 95° C. at a stirring speed of about 200 rpm, employing a heating rate of 45° C./h. Gel is formed within 30 minutes after the internal temperature has reached 95° C. Following formation of the gel, the heating is switched off and the mixture is stirred for a further 60 minutes.

Next 10.0 g of polydimethylsiloxane having 3-mercaptopropyl groups and a viscosity of 190 mPas at 25° C. and a mercaptan content (SH content) of 0.29 wt % are added as a stopper.

At this point, the batch is divided into two portions of equal size, which undergo separate processing thereafter. One portion is processed without addition of a polyorganosiloxane (3a) containing glucoside radicals; the second portion is worked up using a polyorganosiloxane (3a) containing glucoside radicals.

Added to the first half are 43.2 g of the polydimethylsiloxane having a viscosity of 5 mPas at 25° C., which is used as diluent (4), and the mixture is stirred for 5 minutes with an ULTRA-TURRAX® T 50 at 6000 rpm. This operation is repeated twice more with the same amount of diluent (4) each time. In this way a creamy, transparent gel with a very smooth consistency is obtained, which is suitable for use in cosmetic products.

The solids content, i.e. the total content of network of MQ resin and the two Si—H-containing organopolysiloxanes, and also the stopper and the catalyst in the diluent (4), after dilution is 16.4 wt %.

The organopolysiloxane gel obtained possesses a viscosity of 107 000 mPas at 25° C.

Added to the second half are 42.3 g of the polydimethylsiloxane having a viscosity of 5 mPas at 25° C., which is used as diluent (4), and the mixture is stirred for 5 minutes with an ULTRA-TURRAX® T 50 at 6000 rpm. Then 25 g of the organopolysiloxane (3a) containing glucoside radicals from example 14 are added and stirring is continued for 5 minutes with an ULTRA-TURRAX® T 50 at 6000 rpm. In this way a creamy, transparent gel with a very smooth consistency is obtained, which is suitable for use in cosmetic products.

The solids content, i.e. the total content of network of MQ resin and the two Si—H-containing organopolysiloxanes, and also the stopper and the catalyst in the diluent (4), after dilution is 20.5 wt %.

The organopolysiloxane gel obtained possesses a viscosity of 105 000 mPas at 25° C.

According to the evaluation by the panellists, the two resulting organopolysiloxane gels have very good spreadability. The residues were rated as being plentiful and on a majority basis as being predominantly silky and velvety.

The first half of the batch without use of the polyorganosiloxane (3a) containing glucoside radicals is admixed with water and the water is incorporated by stirring using an ULTRA-TURRAX® T 50 at 6000 rpm. In this way it is possible to stir 40 g of water into the resulting gel until saturation occurs. The mixture is observed to be saturated when single fine droplets remain on the surface. This is a sign that the network is saturated with solvent. The gel is now unable to absorb any more water.

The second half of the batch with use of the polyorganosiloxane (3a) containing glucoside radicals is admixed with water and the water is incorporated by stirring using an ULTRA-TURRAX® T 50 at 6000 rpm. In this way it is possible to stir 1200 g of water into the resulting gel until saturation occurs, which can be perceived in the same way as described above.

According to the evaluation by the panellists, the resulting organopolysiloxane gel from the second part of the batch using the polyorganosiloxane (3a) containing glucoside radicals has very good spreadability. The residue was rated as being plentiful and on a majority basis as being predominantly silky and velvety.

Example 2 (Inventive)

A 2000 ml glass reaction vessel is fitted with a condenser with attached nitrogen inlet, heating mantle, anchor stirrer and temperature control. The experiment is performed at a room temperature of 23° C. All of the starting materials possess this temperature.

The reaction vessel is charged with 636 g of a linear trimethylsilyl-terminated polydimethylsiloxane having a viscosity of 2 mPas at 25° C.

Then 18.6 g of an Si—H-containing polydimethylsiloxane of the formula $(Me_3SiO_{1/2})(Me_2SiO_{2/2})_a$ $(MeHSiO_{2/2})_b(Me_3SiO_{1/2})$ are added, with a:b=15:1 and a chain length of a+b=225 repeating units.

Subsequently 100.7 g of a vinyldimethylsiloxy-terminated polydimethylsiloxane of the formula $((H_2C{=}CH)$ $Me_2SiO_{1/2})(Me_2SiO_{2/2})_a((H_2C{=}CH)Me_2SiO_{1/2})$, having a viscosity of 300 $mm^2$ at 25° C. and an iodine number of 4, are added.

Lastly 0.08 g of a mixture of platinum-1,3-divinyl-1,1,3, 3-tetramethyldisiloxane complex in divinyltetramethyldisiloxane is added, the mixture being adjusted such that the added amount corresponds to 5.4 ppm by weight of Pt, based on the sum total of the mass of the vinyldimethylsiloxy-terminated polydimethylsiloxane and the Si—H-containing organopolysiloxane. The reaction vessel is closed and purged with nitrogen for 5 min.

The reaction mixture is subsequently stirred at room temperature at a stirring speed of about 200 rpm. A gel can be seen readily to begin to form after 45 minutes. Following the onset of gel formation, stirring is continued at room temperature for 60 minutes. The final temperature is 38° C., resulting from the exothermicity of the reaction and from the input of heat from stirring.

Next 4.15 g of polydimethylsiloxane having 3-mercaptopropyl groups and a viscosity of 190 mPas at 25° C. and a mercaptan content (SH content) of 0.29 wt % are added as a stopper.

At this point the subsequent procedure is as described in example 1. This means that the batch is divided into two portions of equal size, which are processed further separately from one another.

Added to the first portion are 40.1 g of the polydimethylsiloxane having a viscosity of 2 mPas at 25° C., which is used as diluent (4), and the mixture is stirred for 5 minutes with an ULTRA-TURRAX® T 50 at 6000 rpm. This operation is repeated twice more with the same amount of diluent (4) each time of 40.1 g. No further stopper is added in this case. In this way a creamy, transparent gel with a very smooth consistency is obtained, which is suitable for use in cosmetic products.

The solids content, i.e. the total content of network of vinyl-terminated polysiloxane and the two Si—H-containing organopolysiloxanes, and also the stopper and the catalyst in the diluent (4), after dilution is 12.4 wt %.

The organopolysiloxane gel obtained possesses a viscosity of 97 000 mPas at 25° C.

According to the evaluation by the panellists, the resulting organopolysiloxane gel has very good spreadability. The residue was rated as being plentiful and on a majority basis as being predominantly silky and velvety.

Added to the second portion are 39.6 g of the polydimethylsiloxane having a viscosity of 2 mPas at 25° C. that is used as diluent (4), and also 25.0 g of the organopolysiloxane (3a) containing glucoside radicals, from example 14, which is stirred in for 5 minutes with an ULTRA-TURRAX® T 50 at 6000 rpm. This operation is repeated twice more with the same amount of diluent (4) in each case, of 39.6 g. No further stopper or polyorganosiloxane containing glucoside radical is added. In this way a creamy, transparent gel with very smooth consistency is obtained, which is suitable for use in cosmetic products.

The solids content, i.e. the total content of network of vinyl-terminated polysiloxane and the two Si—H-containing organopolysiloxanes, and also the stopper and the catalyst in the diluent (4), after dilution is 13.5 wt %.

The resulting organopolysiloxane gel possesses a viscosity of 94 000 mPas at 25° C.

According to the evaluation by the panellists, the resulting organopolysiloxane gel has very good spreadability. The residue was rated as being plentiful and on a majority basis as being predominantly silky and velvety.

The first half of the batch without use of the polyorganosiloxane (3a) containing glucoside radicals is admixed with water and the water is incorporated by stirring using an ULTRA-TURRAX® T 50 at 6000 rpm. In this way it is possible to stir 45 g of water into the resulting gel until saturation occurs. The mixture is observed to be saturated when single fine droplets remain on the surface. This is a sign that the network is saturated with solvent. The gel is now unable to absorb any more water.

The second half of the batch with use of the polyorganosiloxane (3a) containing glucoside radicals is admixed with water and the water is incorporated by stirring using an ULTRA-TURRAX® T 50 at 6000 rpm. In this way it is possible to stir 1200 g of water into the resulting gel until saturation occurs, which can be perceived in the same way as described above.

According to the evaluation by the panellists, the resulting organopolysiloxane gel from the second part of the batch using the polyorganosiloxane (3a) containing glucoside radicals has very good spreadability. The residue was rated as being plentiful and on a majority basis as being predominantly silky and velvety.

Example 3 (Inventive)

The procedure corresponds substantially to that described in example 2. In contrast to example 2, the diluent (4) used, rather than a volatile trimethylsilyl-terminated linear polydimethylsiloxane having a viscosity of 2 mPas at 25° C., is a nonvolatile trimethylsilyl-terminated linear polydimethylsiloxane having a viscosity of 5 mPas at 25° C. The amount of diluent (4) charged to the reaction vessel is 780.0 g.

Here, 40.0 g of the Si—H-containing polydimethylsiloxane also used in example 2 are weighed in. Additionally an Si—H-containing polydimethylsiloxane is weighed in, in an amount of 156.0 g, the formula thereof being $(Me_3SiO_{1/2})(Me_2SiO_{2/2})_a(MeHSiO_{2/2})_b(Me_3SiO_{1/2})$ with a:b=15:1 and a chain length of 75 repeating units including the terminal groups. Instead of the vinyl-terminated polydimethylsiloxane from example 2, 6.0 g of hexadiene are used. Added lastly is 0.04 g of a mixture of platinum-1,3-divinyl-1,1,3,3-tetramethyldisiloxane complex in divinyltetramethyldisiloxane, the mixture being adjusted such that the amount added corresponds to 20 ppm by weight of Pt, based on the sum of the mass of the hexadiene and of the two Si—H-containing polydimethylsiloxanes.

For stopping, 14.0 g of polysiloxane having 3-mercaptopropyl groups and a viscosity of 190 mPas at 25° C. and a mercaptan content (SH content) of 0.29 wt % are added as a stopper.

The mixture is stirred for 5 minutes with an ULTRA-TURRAX® T 50 at 6000 rpm to give a creamy, transparent gel with very smooth consistency, which is suitable for use in cosmetic products.

The final solids content, i.e. the content of network composed of the Si—H-containing polydimethylsiloxanes and the hexadiene, together with the amount of catalyst used and the stopper oil, is 21.6 wt %. The viscosity of the resulting organopolysiloxane gel is 360 000 mPas.

At this point the procedure is also in principle as described in example 1. That is, the batch is divided into two portions of equal size, which are processed further separately from one another.

According to the evaluation by the panellists, the resulting organopolysiloxane gel has very good spreadability. The residue was rated as being plentiful and on a majority basis as being dry, silky and velvety.

Added to the second portion are 25.0 g of the organopolysiloxane (3a) containing glucoside radicals, from example 14, and the stopper and the polyorganosiloxane (3b) containing polyglucoside radicals are incorporated by stirring for 5 minutes with an ULTRA-TURRAX® T 50 at 6000 rpm. In this way a creamy, transparent gel with very smooth consistency is obtained, which is suitable for use in cosmetic products.

The solids content, i.e. the total content of network of hexadiene and the two Si—H-containing organopolysiloxanes, and also the stopper and the catalyst in the diluent (4), after dilution is 22.2 wt %.

The resulting organopolysiloxane gel possesses a viscosity of 240 000 mPas at 25° C.

According to the evaluation by the panellists, the resulting organopolysiloxane gel has very good spreadability. The residue was rated as being plentiful and on a majority basis as being predominantly silky and velvety.

The first half of the batch without use of the polyorganosiloxane (3a) containing glucoside radicals is admixed with water and the water is incorporated by stirring using an ULTRA-TURRAX® T 50 at 6000 rpm. In this way it is possible to stir 45 g of water into the resulting gel until saturation occurs. The mixture is observed to be saturated when single fine droplets remain on the surface. This is a sign that the network is saturated with solvent. The gel is now unable to absorb any more water.

The second half of the batch with use of the polyorganosiloxane (3a) containing glucoside radicals is admixed with water and the water is incorporated by stirring using an ULTRA-TURRAX® T 50 at 6000 rpm. In this way it is possible to stir 635 g of water into the resulting gel until saturation occurs, which can be perceived in the same way as described above.

According to the evaluation by the panellists, the resulting organopolysiloxane gel from the second part of the batch using the polyorganosiloxane (3a) containing glucoside radicals has very good spreadability. The residue was rated as being plentiful and on a majority basis as being predominantly silky and velvety.

Example 4: (Comparative Example, not Inventive)

Identical reworking of example 8 from US2016311980A1, using method B.

Example 5: (Inventive) Production of a Hydrophobic Gel Analogous to the Composition Under Example 4, and Addition of the Polyorganosiloxane (3b) Containing Polyglucoside Radicals from Example 14 in the Homogenizing Step The procedure for producing a hydrophobic gel takes place in analogy to example 1. In other words, in contrast to example 4, there is no hydrosilylation step performed on a hydrophilic component; instead, only the hydrophobic components are hydrosilylated, in other words the two H-siloxane equilibrates and the MQ resin in the diluent stipulated by example 4 or example 8 from =US2016311980A1. In this case the amount of (2-allyloxyethoxy)glucoside as per U.S. Pat. No. 5,831,080 example 1 (A) (column 8, lines 23-43), which possesses an iodine number of 29.2, is replaced by the iodine-equivalent amount of MQ resin, with the MQ resin possessing an iodine number of 18 and being the same MQ resin as already used for example 1. It should be borne in mind here that the amount of (2-allyloxyethoxy) glucoside specified in example 8 of US2016311980A1 is only 50% (2-allyloxyethoxy) glucoside and 50% 1,2-propanediol.

Iodine equivalent here means that the amount of MQ resin as a substitute for the (2-allyloxyethoxy) glucoside is selected such that the amount of vinyl groups for the hydrosilylation is the same as for example 4. The amount of (2-allyloxyethoxy) glucoside is therefore replaced by [(29.2: 2):18] times the amount of MQ resin.

Moreover, in deviation from the procedure in example 1, a heating rate of 90° C./hour is selected, it being known from the teaching of WO2018228657A that it is otherwise impossible to obtain a high-viscosity gel from the selected H-siloxane equilibrates according to example 4. In example 4 or example 8 from US2016311980A1, this is compensated by adding the MQ resin at 95° C., in other words at the highest reaction temperature corresponding to a theoretical infinitely high heating rate.

In contrast to example 1, the two Si—H-containing polyorganosiloxanes are used in the same ratio and in the same amount as they were used for example 4.

In addition, the catalyst and the stopper are selected, in terms of their nature and amount, in accordance with example 4: the catalyst is added not in two portions as per example 4, but instead all at once in line with the procedure from example 1.

The nature of the diluent (4) chosen corresponds to the procedure as per example 4, although used at 10 weight percent less.

Together with the stopper, 25.0 g of the polyorganosiloxane (3b) containing polyglucoside radicals from example 14 are added, and are incorporated together with the stopper using a Turrax in accordance with the example 4 procedure.

The two organopolysiloxane gels as per example 4 and example 5 are compared with one another for their cosmetically relevant properties and their appearance.

The organopolysiloxane gel from example 4 is a creamy, sag-resistant, storage-stable, translucent elastomer gel having a viscosity of 102 000 mPas. In other words, it is not clear.

The organopolysiloxane gel from example 5 is a transparent organopolysiloxane gel having a viscosity of 110 000 mPas.

The table below shows the gel/water ratio which can be absorbed up to saturation:

|  | Example 4 | Example 1 with (3a) |
| --- | --- | --- |
| Gel:water ratio | 1:0.7 | 1:2.45 |

The organopolysiloxane gel obtained from example 4 is admixed with water and the water is incorporated by stirring using an ULTRA-TURRAX® T 50 at 6000 rpm. In this way it is possible to incorporate 350 g of water into the resulting gel until saturation occurs. A saturated mixture is apparent from the single fine droplets lying on the surface. This is a sign that the network is saturated with solvent. The gel is now no longer able to absorb any more water.

The organopolysiloxane gel obtained from example 5 is admixed with water and the water is incorporated by stirring using an ULTRA-TURRAX® T 50 at 6000 rpm. In this way it is possible to incorporate 1225 g of water into the resulting gel by stirring until saturation occurs, saturation being apparent in the same way as described above.

According to the evaluation by the panellists, the organopolysiloxane gels of example 4 and example 5 are both very suitable for use in cosmetic products. They have very good spreadability. The residue was rated in each case as being plentiful and on a majority basis as being predominantly silky and velvety, with the organopolysiloxane gel from example 5 showing advantages in terms of spreadability and of plentifulness. The organopolysiloxane gel of example 5 was also rated as being somewhat more velvety.

Example 6: (Comparative Example, not Inventive)

Identical reworking of example 1 from US20160317427A1, using method B.

Example 7: (Inventive: Production of a Hydrophobic Gel According to Example 6 and Addition of a Polyorganosiloxane Comprising Polyglycol Radicals During Homogenization)

The procedure for producing a hydrophobic gel takes place in analogy to example 1. In other words, in contrast to example 6, there is no hydrosilylation step performed on a hydrophilic component; instead, only the hydrophobic components are hydrosilylated, in other words the two H-siloxane equilibrates and the MQ resin in the diluent stipulated by example 6 or example 1 from US20160317427A1. In this case the amount of polyoxyethylated allyl alcohol, which possesses an iodine number of about 52.5, is replaced by the iodine-equivalent amount of MQ resin, with the MQ resin possessing an iodine number of 18 and being the same MQ resin as already used for example 1. Iodine equivalent here means that the amount of MQ resin as a substitute for the polyoxyethylated allyl alcohol is selected such that the amount of vinyl groups for the hydrosilylation is the same as for example 6. The amount of polyoxyethylated allyl alcohol is therefore replaced by (52.5:18) times the amount of MQ resin. Moreover, in deviation from the procedure in example 1, a heating rate of 90° C./hour is selected, it being known from the teaching of WO2018228657A that it is otherwise impossible to obtain a high-viscosity gel from the selected H-siloxane equilibrates according to example 6. In example 6 or example 1 from US20160317427A1, this is compensated by adding the MQ resin at 95° C., in other words at the highest reaction temperature corresponding to a theoretical infinitely high heating rate.

In contrast to example 1, the two Si—H-containing polyorganosiloxanes are used in the same ratio and in the same amount as they were used for example 6.

In addition, the catalyst and the stopper are selected, in terms of their nature and amount, in accordance with example 6: the catalyst is added not in two portions as per example 6, but instead all at once in line with the procedure from example 1.

The nature of the diluent (4) chosen corresponds to the procedure as per example 6, although used at 10 weight percent less.

Together with the stopper, 25.0 g of the polyorganosiloxane containing polyoxyethylene radicals from example 15 are added, and are incorporated together with the stopper using a Turrax in accordance with the example 6 procedure.

It should be noted at this point that the hydrophobic gels, prior to addition of the polyorganosiloxane (3a) containing polyglucoside radicals as per example 14 or, respectively, of the polyorganosiloxane carrying polyoxyethylated radicals from example 15, are the same.

In the case of a procedure in accordance with the invention, therefore, it would be possible to use either the two hydrophilic gels or the hydrophobic base gel, thus giving 3 instead of only 2 saleable products. Moreover, the hydrophobic base gel can be given different performance features according to the selection of the admixture component chosen.

The two organopolysiloxane gels as per example 6 and example 7 are compared with one another for their cosmetically relevant properties and their appearance.

The organopolysiloxane gel from example 6 is a creamy, sag-resistant, storage-stable, transparent elastomer gel having a viscosity of 142 000 mPas.

The organopolysiloxane gel from example 7 is a transparent organopolysiloxane gel having a viscosity of 131 000 mPas.

The table below shows the gel/water ratio which can be absorbed up to saturation:

|  | Example 1 with (3a) | Example 6 | Example 7 |
| --- | --- | --- | --- |
| Gel:water | 1:2.45 | 1:<0.1 | 1:<0.1 |

The organopolysiloxane gel obtained from example 6 is admixed with water and the water is incorporated by stirring using an ULTRA-TURRAX® T 50 at 6000 rpm. In this way it is possible to incorporate 40 g of water into the resulting gel until saturation occurs. A saturated mixture is apparent from the single fine droplets lying on the surface. This is a sign that the network is saturated with solvent. The gel is now no longer able to absorb any more water.

The organopolysiloxane gel obtained from example 7 is admixed with water and the water is incorporated by stirring using an ULTRA-TURRAX® T 50 at 6000 rpm. In this way it is possible to incorporate 45 g of water into the resulting gel by stirring until saturation occurs, saturation being apparent in the same way as described above.

According to the evaluation by the panellists, the organopolysiloxane gels of example 6 and example 7 are both very suitable for use in cosmetic products. They have very good spreadability. The residue was rated in each case as being plentiful and on a majority basis as being predominantly silky and velvety, with all of these properties being more pronounced in the case of the organopolysiloxane gel from example 7. With regard in particular to the spreading and plentifulness, the organopolysiloxane gel of example 7 possesses significant advantages over the organopolysiloxane gel from example 6.

Example 8: (Comparative Example, not Inventive: Production of a Cyclodextrin-Based Hydrophilic Elastomer Gel)

Identical reworking of example 1 from WO2020139403A1.

Example 9: (Inventive: Production of a Hydrophobic Gel According to Example 6 and Addition of a Polyorganosiloxane (3c) Comprising Cyclodextrin Radicals During Homogenization)

The procedure for producing a hydrophobic gel takes place in analogy to example 1. In other words, in contrast to example 8, there is no hydrosilylation step performed on a hydrophilic component; instead, only the hydrophobic components are hydrosilylated, in other words the H-siloxane equilibrate and the MQ resin in the diluent (4) stipulated by example 8 or example 1 from WO2020139403A1. In this case the amount of allylcyclodextrin, which possesses 2.66 mol % of allyl groups, is replaced by the olefin-equivalent amount of MQ resin, with the MQ resin containing 5 mol % of vinyl groups. Note here that the allylcyclodextrin as per example 1 according to WO2020139403A1 or the example of the present invention is added as a 50% solution in isopropanol. Olefin equivalent here means that the amount of MQ resin as a substitute for the allylcyclodextrin as per example 1 from WO2020139403A1 is selected such that the amount of vinyl groups for the hydrosilylation is the same as the number of allyl groups for example 1 of WO2020139403A1 or example 8 of this invention. The amount of allylcyclodextrin is therefore replaced by [(2.66:2):5] times the amount of MQ resin.

Moreover, in deviation from the procedure in example 1 of the present invention, a heating rate of 90° C./hour is selected, it being known from the teaching of WO2018228657A that it is otherwise impossible to obtain a high-viscosity gel from the selected H-siloxane equilibrate according to example 8 of the present invention or example 1 as per WO2020139403A1. In example 8 of the present invention or example 1 from WO2020139403A1 this is compensated by adding the MQ resin at 80° C., in other words at the highest reaction temperature corresponding to a theoretical infinitely high heating rate.

In contrast to example 1 of the present invention, the Si—H-containing polyorganosiloxane and also the MQ resin are used in the same ratio and in the same amount as they were used for example 8 of the present invention or example 1 as per WO2020139403A1.

In addition, the catalyst, the diluent (4) and the stopper are selected, in terms of their nature and amount, in accordance with example 8 of the present invention: the catalyst is added not in two portions as per example 8, but instead all at once in line with the procedure from example 1 of the present invention.

Together with the stopper, 7.5 g of the polyorganosiloxane (3c) containing cyclodextrin radicals from example 16 are added, and are incorporated together with the stopper using a Turrax in accordance with the example 8 procedure.

The two organopolysiloxane gels as per example 8 and example 9 are compared with one another for their cosmetically relevant properties and their appearance.

The organopolysiloxane gel from example 8 is a creamy, sag-resistant, storage-stable, translucent, i.e. non-transparent elastomer gel having a viscosity of 63 000 mPas.

The organopolysiloxane gel from example 9 is a transparent organopolysiloxane gel having a viscosity of 72 000 mPas.

The organopolysiloxane gel obtained from example 8 is admixed with water and the water is incorporated by stirring using an ULTRA-TURRAX® T 50 at 6000 rpm. In this way it is possible to incorporate 250 g of water into the resulting gel until saturation occurs. A saturated mixture is apparent from the single fine droplets lying on the surface. This is a sign that the network is saturated with solvent. The gel is now no longer able to absorb any more water.

The organopolysiloxane gel obtained from example 9 is admixed with water and the water is incorporated by stirring using an ULTRA-TURRAX® T 50 at 6000 rpm. In this way it is possible to incorporate 300 g of water into the resulting gel by stirring until saturation occurs, saturation being apparent in the same way as described above.

The Table Below Shows the Gel/Water Ratio which can be Absorbed Up to Saturation:

|  | Example 1 with (3a) | Example 8 | Example 9 |
|---|---|---|---|
| Gel:water | 1:2.45 | 1:0.5 | 1:0.6 |

According to the evaluation by the panellists, the organopolysiloxane gels of example 8 and example 9 are both very suitable for use in cosmetic products. They have very good spreadability. The residue was rated in each case as being plentiful and on a majority basis as being predominantly silky and velvety, with the organopolysiloxane gel of example 9 showing advantages in terms of spreadability and of plentifulness. The organopolysiloxane gel from example 9 was also rated as being somewhat more velvety.

Example 10: (Inventive)

A hydrophobic organopolysiloxane gel is produced according to the procedure in example 5. In deviation from the procedure in example 5, in this example, together with the stopper, the polyorganosiloxane added is not the polyorganosiloxane (3b) containing polyglucoside radicals, but rather the polyorganosiloxane (3c) containing cyclodextrin radicals from example 16.

The resulting organopolysiloxane gel is admixed with water and the water is incorporated by stirring using an ULTRA-TURRAX® T 50 at 6000 rpm. It is possible in this way to incorporate 1400 g of water into the resulting gel by stirring until saturation occurs, this being apparent in the same way as described above.

According to the evaluation by the panellists, the resulting organopolysiloxane gel is highly comparable, in terms of its properties relevant for cosmetic applications, with the gel obtained using the polyorganosiloxane (3a) containing glucoside radicals as per example 5. The gel has very good spreadability. The residue was rated as being plentiful and on a majority basis as being predominantly silky and velvety.

In contrast to the organopolysiloxane gel of example 5, it is easier to spread and the residue is somewhat more plentiful.

It should be noted at this point that the hydrophobic gel in this example is the same as in example 5 and example 7. From just one hydrophobic base gel, accordingly, it is possible to produce a spectrum of hydrophilic gels, with the hydrophobic base gel itself already possessing good cosmetic properties and being suitable for use itself as a commercial product. It should also be noted that the amount of hydrophilic additions is comparatively low, and so the amount of one production batch yields a correspondingly large amount of hydrophilic organopolysiloxane gel preparations. At a low load on the production unit used for providing the hydrophilic polyorganosiloxanes therefore, a correspondingly large amount of different organopolysiloxane gels are obtained, all of which are based on the same chemical platform for the organopolysiloxane gel. For the production site producing the organopolysiloxane gel, this results in a saving in logistics and in storage facilities for the holding of a wide range of different raw materials. The number of metering devices and the number of different operating steps are reduced and consequently the robustness of the process as a whole is increased, and the susceptibility to error is significantly reduced.

Example 11: (not Inventive: Addition of the Sugar, the Allyl-PEG and the Allyl-CD without Siliconization)

Incorporated into 98.5 g of the hydrophobic organopolysiloxane gel as per example 1 of the present invention, instead of the polyorganosiloxane containing polyglucoside groups but at the same point, are the following amounts of the alkenylglucoside of example 12 or of the polyoxyethylated allyl alcohol $H_2C=CH—CH_2—(OC_2H_4)_{10}—OH$ as per example 6, obtainable under the name polyglycol A 500 from Clariant, or of the allylcyclodextrin as per example 13:

| | |
|---|---|
| Alkenylglucoside | 1.5 g |
| Polyoxyethylated allyl alcohol | 1.5 g |
| Allylcyclodextrin | 1.5 g |

The preparations obtained are all cloudy.

Water is incorporated into the resulting preparations by a procedure analogous to that described for example 1.

The preparations prove to be unstable; the amounts of water which can be incorporated are set out in the table below:

| | Example 1 with (3a) | Example 1 without (3a) + alkenyl-glucoside | Example 1 without (3a) + polyoxyethylated allyl alcohol | Example 1 without (3a) + allyl-cyclodextrin |
|---|---|---|---|---|
| Gel:water | 1:2.45 | 1:<0.1 | 1:<0.1 | 1:0.1 |

Example 12: Preparation of the Alkenylglucoside for the Synthesis of the Polyorganosiloxane (3b) Containing Polyglucoside Radicals The alkenylglucoside for preparing the polyorganosiloxane containing polyglucoside radicals, employed here in the examples, was prepared by the process described in U.S. Pat. No. 5,831,080 in example 1 (A) (column 8, lines 23-43), with the difference that the solvent is not distilled off completely in the last step, since that would lead to a material which was glasslike at room temperature; instead, a solvent switch to 1,2-propanediol is carried out. The product is an approximately 50% solution of the alkenylglucoside in 1,2-propanediol.

Example 13: Preparation of the Allylcyclodextrin

The allylcyclodextrin is prepared according to WO2020139403A1 protocol "Synthesis of allyl modified methyl β-cyclodextrin" [0054-0055].

Example 14: Preparation of a Polyorganosiloxane (3b) Containing Polyglucoside Radicals A 20 l glass stirring unit with metering and distillation equipment and steam-operated heating jacket is charged with 2235 g of $(Me_3SiO_{1/2})(Me_2SiO_{2/2})_a(MeHSiO_{2/2})_b$ $(Me_3SiO_{1/2})$, with a:b=9:1 and a chain length of a+b=60 repeating units, and this initial charge is preheated to 100° C. It is stirred at a rate of 70 revolutions per minute. Metered into this initial charge are 789 g of a preparation of the alkenylglucoside solution from example 12, hexachloroplatinic acid in isopropanol, and aqueous potassium hydroxide solution, over the course of 6 hours.

The preparation is prepared as follows: 789 g of the alkenylglucoside solution from example 12 are heated to 60° C. in a heating cabinet. 10 ml of the heated solution are withdrawn and mixed with 0.224 g of a 50% aqueous solution of potassium hydroxide. This mixture is reintroduced into the rest of the alkenylglucoside solution, with thorough mixing. 0.18 g of hexachloroplatinic acid is dissolved in 18.61 g of isopropanol. This solution is added to the mixture of potassium hydroxide and alkenylglucoside solution, with thorough mixing.

The resulting preparation is metered as described above. During metering the heating is shut off.

After the end of metering, a solution of 0.093 g of hexachloroplatinic acid and 9.3 g of isopropanol is added to the reaction vessel, with mixing. The internal temperature is raised to 120° C. by heating, and this temperature is maintained for 2 h. The heating is subsequently shut off and cooling takes place to 110° C. 29 g of octadec-1-ene are metered in without heating.

The reaction mixture undergoes slight heating to 113° C. It is heated again to 120° C. and this temperature is maintained for 2 h. Subsequently cooling takes place to 60° C.

Thereafter 6.51 kg of a linear polydimethylsiloxane having a viscosity of 5 mPas are added rapidly and mixed thoroughly. The temperature in the stirring unit is raised to 130° C. and reduced pressure is applied. A mixture of isopropanol, 1,2-propanediol and low-boiling siloxane fractions is distilled off until a final vacuum of 5 mbar is reached.

When distillate is no longer obtained under these conditions, the reduced pressure is broken and cooling takes place to 30° C. Subsequently 22 g of a 35% hydrogen peroxide solution are added, and the temperature is raised to 60° C. by heating, where it is held for 1 h.

After that, cooling takes place to 23° C. and the contents of the reaction vessel are filtered through a 25 μm filter, to give 8.7 kg of a clear, substantially colourless or at very most slightly yellowish filtrate.

This preparation is used in the as-obtained form as polyorganosiloxane (3b) containing polyglucoside radicals. All of the amounts in the examples are based on this preparation.

By virtue of its composition, the active ingredient obtained has an HLB of around 7. The preparation contains 30 weight percent of this ingredient.

Example 15: Preparation of the PEG Oil

The polyorganosiloxane containing polyoxyethylene units is prepared by a procedure analogous to that described in example 14.

In contrast to example 14, instead of the alkenylglucoside in 1,2-propanediol as per example 12, the polyoxyethylated allyl alcohol $H_2C\!=\!CH\!-\!CH_2\!-\!(OC_2H_4)_{10}\!-\!OH$ is used here. Instead of 789 g of the alkenyl glucoside in 1,2-propanediol, containing 394.5 g of alkenyl glucoside, 1420 g are used here of a mixture of 710 g of the polyoxylated allyl alcohol with 710 g of 1,2-propanediol. This mixture is mixed at room temperature with the same amount of hexachloroplatinic acid in isopropanol as indicated in example 14. No aqueous potassium hydroxide solution is used. Otherwise, the initial-charge quantities and metering quantities and also the metering times and temperatures remain the same.

The amount of hexachloroplatinic acid in isopropanol for subsequent metering is also the same. This synthesis ends after the hydrosilylation of the octadec-1-ene. In other words, the bleaching step with hydrogen peroxide is not carried out here. Following the distillation, as described above, discharge takes place through a 25 μm filter to give a clear, colourless solution which contains around 32 weight percent of the polyorganosiloxane active ingredient containing polyglycol radicals, as a solution in the linear polyorganosiloxane with a viscosity of 5 mPas.

Example 16: Preparation of the CD Oil

The polyorganosiloxane (3c) containing cyclodextrin radicals is prepared by a procedure analogous to that described in example 14.

In contrast to example 14, instead of the alkenylglucoside in 1,2-propanediol as per example 12, the allyl-modified β-cyclodextrin as per example 13 is used here.

For the hydrosilylation, 394.5 g of a 50% solution of the β-cyclodextrin of example 13 in 1,2-propanediol are used.

The steps are otherwise formed in accordance with the procedure of example 14.

The result is an around 30 weight percent solution of the polyorganosiloxane (3c) containing cyclodextrin radicals in the linear polydimethylsiloxane with the viscosity of 5 mPas.

The invention claimed is:

1. Hydrophilic organopolysiloxane gel preparation, comprising:

wherein the hydrophilic organopolysiloxane gel preparation comprises a mixture (X) and at least one diluent (4) for viscosity adjustment, wherein the mixture (X) comprises (a) 80 to 99.9 wt % of at least one hydrophobic organopolysiloxane gel prepared from the reaction either of an unsaturated organopolysiloxane resin (1a) or of an unsaturated organopolysiloxane (1b) or of a diene (1c) with an Si—H-containing organopolysiloxane (2a) optionally in the mixture with an Si—H-containing organopolysiloxane (2b) in the presence of a catalyst (K) which promotes the addition of Si-bonded hydrogen onto aliphatic multiple bond (i.e. hydrosilylation catalyst) in the presence of a diluent (4), the reaction being stopped by addition of a stopper compound (5) which is used as a catalyst poison and which remains in the hydrophobic organopolysiloxane gel;

(b) 0.1 to 20 wt % of at least one compound (3), wherein the at least one compound (3) is (3a) organopolysiloxanes containing glycoside radicals and of the general formula (V), (3c) organopolysiloxanes containing cyclodextrin radicals and of the formula (VII), or a combination thereof;

wherein the general formula (V) is $$R_h R^3{}_i SiO_{(4-h-i)/2} \qquad (V);$$

wherein R may be identical or different and is a monovalent, optionally substituted hydrocarbon radical having 1 to 18 carbon atoms per radical, with exclusion of heteroatoms and hetero groups which would hinder a hydrosilylation reaction by adversely affecting the catalyst;

wherein $R^3$ may be identical or different and is a radical of the formula $$Z\!-\!(R^4O)_j\!-\!R^5\!- \qquad (Va);$$

wherein Z is a glycoside radical composed of 1 to 10 monosaccharide units;

wherein $R^4$ may be identical or different and is a divalent hydrocarbon radical having 2 to 4 carbon atoms;

wherein j is 0 or an integer from 1 to 20;

wherein $R^5$ may be identical or different and is a divalent hydrocarbon radical having 2 to 12 carbon atoms;

wherein h and i are each 0, 1, 2 or 3, with the proviso that h+i≤3 and in at least one repeating unit i has a value of at least 1;

wherein the formula (VII) is $$R_h R^9{}_i SiO_{(4-h-i)/2} \qquad (VII);$$

wherein R may have the definitions indicated above;

wherein $R^9$ may be identical or different and is a radical of the formula $$C\!-\!R^{10}\!- \qquad (VIIa);$$

wherein C is a cyclodextrin radical of the form

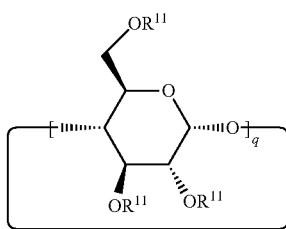

wherein $R^{11}$ is a hydrogen radical or a methyl radical;

wherein q is the integers 6 (alpha cyclodextrin), 7 (beta cyclodextrin) or 8 (gamma cyclodextrin);

wherein $R^{10}$ is a divalent hydrocarbon radical having 2 to 18 carbon atoms which is optionally interrupted with heteroatoms;

wherein h and i each have the definition indicated earlier on above;

where the sum of the mixture (X) always makes 100 wt %;

wherein the at least one diluent (4) is different from (3a) and (3c); and wherein the hydrophilic organopolysiloxane gel preparation exhibits an increase in the water absorption capacity by at least a factor of 10, compared with the hydrophobic organopolysiloxane gel used.

2. The preparation of claim 1, wherein the compound (3) is only selected from the group of the compounds (3a).

3. The preparation of claim 1, wherein the compound (3) is only selected from the group of the compounds (3c).

4. The preparation of claim 1, wherein the hydrophobic organopolysiloxane gel is selected from those obtained by the following reaction:

reaction of unsaturated organopolysiloxane resins (1a) with Si—H-functional crosslinkers (2a), in the presence or absence of Si—H-containing organopolysiloxanes (2b) and in the presence of a catalyst (K); and stopping of the reaction by addition of a stopper compound (5) used as a catalyst poison.

5. The preparation of claim 1, wherein the preparation is used in a cosmetic preparation or preparation for body care and health care, a washing and cleaning preparation, a preparation for long-lasting fragrancing or an insect repellency.

6. The preparation of claim 1, wherein the preparation is used as a filler or insulating material for electrical cables, soil or water barriers for soil stabilization, or as substitute for epoxy materials which are used in components in the electronics industry.

7. Method for producing a hydrophilic organopolysiloxane gel preparation, comprising:

combining a mixture (X) and at least one diluent (4) for viscosity adjustment, wherein the mixture (X) comprises (a) 80 to 99.9 wt % of at least one hydrophobic organopolysiloxane gel prepared from the reaction either of an unsaturated organopolysiloxane resin (1a) or of an unsaturated organopolysiloxane (1b) or of a diene (1c) with an Si—H-containing organopolysiloxane (2a) optionally in the mixture with an Si—H-containing organopolysiloxane (2b) in the presence of a catalyst (K) which promotes the addition of Si-bonded hydrogen onto aliphatic multiple bond (i.e. hydrosilylation catalyst) in the presence of a diluent (4), the reaction being stopped by addition of a stopper compound (5) which is used as a catalyst poison and which remains in the hydrophobic organopolysiloxane gel, (b) 0.1 to 20 wt % of at least one compound (3), wherein the at least one compound (3) is (3a) organopolysiloxanes containing glycoside radicals and of the general formula (V), (3c) organopolysiloxanes containing cyclodextrin radicals and of the formula (VII), or a combination thereof, wherein the general formula (V) is $$R^h R^3_i SiO_{(4-h-i)/2} \qquad (V),$$

wherein R may be identical or different and is a monovalent, optionally substituted hydrocarbon radical having 1 to 18 carbon atoms per radical, with exclusion of heteroatoms and hetero groups which would hinder a hydrosilylation reaction by adversely affecting the catalyst, wherein $R^3$ may be identical or different and is a radical of the formula $$Z—(R^4O)_j—R^5— \qquad (Va),$$

wherein Z is a glycoside radical composed of 1 to 10 monosaccharide units, wherein $R^4$ may be identical or different and is a divalent hydrocarbon radical having 2 to 4 carbon atoms, wherein j is 0 or an integer from 1 to 20, wherein $R^5$ may be identical or different and is a divalent hydrocarbon radical having 2 to 12 carbon atoms, wherein h and i are each 0, 1, 2 or 3, with the proviso that h+i≤3 and in at least one repeating unit i has a value of at least 1;

wherein the formula (VII) is $$R_h R^9_i SiO_{(4-h-i)/2} \qquad (VII);$$

wherein R may have the definitions indicated above, wherein $R^9$ may be identical or different and is a radical of the formula $$C—R^{10}— \qquad (VIIa);$$

wherein C is a cyclodextrin radical of the form

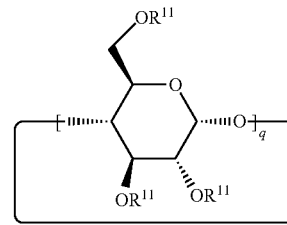

wherein $R^{11}$ is a hydrogen radical or a methyl radical, wherein q is the integers 6 (alpha cyclodextrin), 7 (beta cyclodextrin) or 8 (gamma cyclodextrin), wherein $R^{10}$ is a divalent hydrocarbon radical having 2 to 18 carbon atoms which is optionally interrupted with heteroatoms, wherein h and i each have the definition indicated earlier on above;

where the sum of the mixture (X) always makes 100 wt %, and wherein the at least one diluent (4) is different from (3a) and (3c), wherein the hydrophilic organopolysiloxane gel preparation exhibits an increase in the water absorption capacity by at least a factor of 10 compared with the hydrophobic organopolysiloxane gel used.

8. The preparation of claim 1, wherein the preparation is used in cosmetic preparations or preparations for body care and health care, or in washing and cleaning products, or in products for long-lasting fragrancing or insect repellency.

9. The preparation of claim 1, wherein the preparation is used as a filler or insulating material for electrical cables, soil or water barriers for soil stabilization, or as substitute for epoxy materials which are used in components in the electronics industry.

10. The preparation of claim 1, wherein the mixture (X) is present in an amount of 2 to 80 wt % and the at least one diluent (4) is present in an amount of 20 to 98 wt %; and wherein the sum of the mixture (X) and the diluent (4) always makes 100 wt % of the hydrophilic organopolysiloxane gel preparation.

11. The method of claim 7, wherein the mixture (X) is present in an amount of 2 to 80 wt % and the at least one diluent (4) is present in an amount of 20 to 98 wt %; and wherein the sum of the mixture (X) and the diluent (4) always makes 100 wt % of the hydrophilic organopolysiloxane gel preparation.

12. The method of claim 7, wherein the compound (3) is only selected from the group of the compounds (3a).

13. The method of claim 7, wherein the compound (3) is only selected from the group of the compounds (3c).

14. The method of claim 7, wherein the hydrophobic organopolysiloxane gel is selected from those obtained by the following reaction:

reaction of unsaturated organopolysiloxane resins (1a) with Si—H-functional crosslinkers (2a), in the presence or absence of Si—H-containing organopolysiloxanes (2b) and in the presence of a catalyst (K); and stopping of the reaction by addition of a stopper compound (5) used as a catalyst poison.

15. Hydrophilic organopolysiloxane gel preparation, comprising:

wherein the hydrophilic organopolysiloxane gel preparation comprises a mixture (X) and at least one diluent (4) for viscosity adjustment, wherein the mixture (X) comprises (a) 80 to 99.9 wt % of at least one hydrophobic organopolysiloxane gel prepared from the reaction either of an unsaturated organopolysiloxane resin (1a) or of an unsaturated organopolysiloxane (1b) or of a diene (1c) with an Si—H-containing organopolysiloxane (2a) optionally in the mixture with an Si—H-containing organopolysiloxane (2b) in the presence of a catalyst (K) which promotes the addition of Si-bonded hydrogen onto aliphatic multiple bond (i.e. hydrosilylation catalyst) in the presence of a diluent (4), the reaction being stopped by addition of a stopper compound (5) which is used as a catalyst poison and which remains in the hydrophobic organopolysiloxane gel;

(b) 0.1 to 20 wt % of at least one compound (3), wherein the at least one compound (3) is (3c) organopolysiloxanes containing cyclodextrin radicals and of the formula (VII);

wherein the formula (VII) is $$R^h R^9{}_i SiO_{(4-h-i)/2} \tag{VII};$$

wherein R may have the definitions indicated above;

wherein $R^9$ may be identical or different and is a radical of the formula $$C—R^{10}— \tag{VIIa};$$

wherein C is a cyclodextrin radical of the form

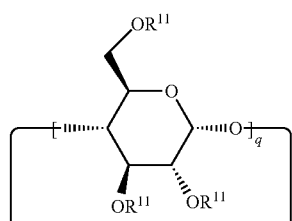

wherein $R^{11}$ is a hydrogen radical or a methyl radical;

wherein q is the integers 6 (alpha cyclodextrin), 7 (beta cyclodextrin) or 8 (gamma cyclodextrin);

wherein $R^{10}$ is a divalent hydrocarbon radical having 2 to 18 carbon atoms which is optionally interrupted with heteroatoms;

wherein h and i each have the definition indicated earlier on above;

where the sum of the mixture (X) always makes 100 wt %;

wherein the at least one diluent (4) is different from (3c); and wherein the hydrophilic organopolysiloxane gel preparation exhibits an increase in the water absorption capacity by at least a factor of 10, compared with the hydrophobic organopolysiloxane gel used.

\* \* \* \* \*